(12) United States Patent
Aronhime et al.

(10) Patent No.: US 7,468,444 B2
(45) Date of Patent: Dec. 23, 2008

(54) CRYSTAL FORMS OF ATORVASTATIN HEMI-CALCIUM AND PROCESSES FOR THEIR PREPARATION AS WELL AS NOVEL PROCESSES FOR PREPARING OTHER FORMS

(75) Inventors: Judith Aronhime, Rehovot (IL); Ramy Lidor-Hadas, Kfar Saba (IL); Valerie Niddam, Even-Yeouda (IL); Revital Lifshitz, Herzlia (IL); Shlomit Wizel, Petah Tiqva (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 11/257,979

(22) Filed: Oct. 24, 2005

(65) Prior Publication Data
US 2006/0058533 A1   Mar. 16, 2006

Related U.S. Application Data

(62) Division of application No. 10/994,142, filed on Nov. 19, 2004, now Pat. No. 7,144,916, which is a division of application No. 09/997,126, filed on Nov. 29, 2001, now abandoned.

(60) Provisional application No. 60/326,529, filed on Oct. 1, 2001, provisional application No. 60/312,144, filed on Aug. 13, 2001, provisional application No. 60/281,872, filed on Apr. 5, 2001, provisional application No. 60/267,897, filed on Feb. 9, 2001, provisional application No. 60/250,072, filed on Nov. 30, 2000.

(51) Int. Cl.
    C07D 207/34   (2006.01)
    A61K 31/40    (2006.01)
(52) U.S. Cl. .................................... 548/537
(58) Field of Classification Search ............ 548/537
    See application file for complete search history.

(56) References Cited

U.S. PATENT DOCUMENTS

| 4,137,322 | A | 1/1979 | Endo et al. |
|---|---|---|---|
| 4,681,893 | A | 7/1987 | Roth |
| 5,003,080 | A | 3/1991 | Butler et al. |
| 5,273,995 | A | 12/1993 | Roth |
| 5,298,627 | A | 3/1994 | Butler et al. |
| 5,686,104 | A | 11/1997 | Mills et al. |
| 5,969,156 | A | 10/1999 | Briggs et al. |
| 6,087,511 | A | 7/2000 | Lin et al. |
| 6,121,461 | A | 9/2000 | McKenzie |
| 6,476,235 | B2 | 11/2002 | Butler et al. |
| 6,528,661 | B2 | 3/2003 | Niddam et al. |
| 6,600,051 | B2 | 7/2003 | Tully |
| 6,605,636 | B2 | 8/2003 | Aronhime et al. |
| 6,605,728 | B2 | 8/2003 | O'Connell et al. |
| 6,605,729 | B1 | 8/2003 | Byrn et al. |
| 2002/0099224 | A1 | 7/2002 | Niddam et al. |
| 2002/0115709 | A1 | 8/2002 | Aronhime et al. |
| 2003/0114686 | A1 | 6/2003 | Van der Schaaf et al. |
| 2003/0212279 | A1 | 11/2003 | Tessler et al. |
| 2003/0216584 | A1 | 11/2003 | Aronhime et al. |
| 2004/0054193 | A1 | 3/2004 | Byrn et al. |
| 2004/0077708 | A1 | 4/2004 | Grahek et al. |
| 2004/0106670 | A1 | 6/2004 | Blatter et al. |
| 2004/0220255 | A1 | 11/2004 | Van Der Schaaf et al. |
| 2004/0242899 | A1 | 12/2004 | Reddy et al. |
| 2005/0209306 | A1 | 9/2005 | Jegorov et al. |
| 2007/0032665 | A1* | 2/2007 | Gudipati et al. ............ 548/537 |

FOREIGN PATENT DOCUMENTS

| WO | WO 97/03960 | 7/1996 |
|---|---|---|
| WO | WO 97/03958 | 2/1997 |
| WO | WO 97/03959 | 2/1997 |
| WO | WO 00/71116 A | 11/2000 |
| WO | WO 02/057228 | 1/2001 |
| WO | WO 01/28999 A | 4/2001 |
| WO | WO 01/36384 | 5/2001 |
| WO | WO 01/42209 A | 6/2001 |
| WO | WO 01/44180 | 6/2001 |
| WO | WO 01/44181 | 6/2001 |
| WO | WO 02/41834 | 5/2002 |
| WO | WO 02/43732 | 6/2002 |
| WO | WO 02/051804 | 7/2002 |
| WO | WO 02/057229 | 7/2002 |
| WO | WO 02/059087 | 8/2002 |
| WO | WO 02/083637 | 10/2002 |
| WO | WO 02/083638 | 10/2002 |
| WO | WO 03/004470 | 1/2003 |
| WO | WO 03/011826 | 2/2003 |
| WO | WO 03/016317 A | 2/2003 |
| WO | WO 03/018547 | 3/2003 |
| WO | WO 03/050085 | 6/2003 |
| WO | WO 03/070702 | 8/2003 |
| WO | WO 2004/022053 | 3/2004 |
| WO | WO 2004/050618 | 6/2004 |

OTHER PUBLICATIONS

Thomas M.A. Bocan et al. "Antiatherosclerotic activity of inhibitors of 3-hydroxy-3-methylglutaryl coenzyme A reductase in cholesterol-fed rabbits: a biochemical and morphological evaluation", Atherosclerosis 111 (1994) pp. 127-142.*

Bang-Chi Chen et al., "Synthesis of Deuterium-Labeled Atorvastatin and its Metabolites for Use as Internal Standards in a LC/MS/MS Method Developed for Quantitation of the Drug and its Metabolites in Human Serum," Journal of Labelled Compounds and Radiopharmaceuticals 43 (2000) pp. 261-270*.

(Continued)

*Primary Examiner*—Fiona T Powers
(74) *Attorney, Agent, or Firm*—Kenyon & Kenyon LLP

(57) ABSTRACT

The present invention provides novel forms of atorvastatin designated Forms VI, VIII, IX, X, XI and XII and novel processes for their preparation as well as processes for preparing atorvastatin Forms I, II, IV, V and amorphous atorvastatin.

8 Claims, 13 Drawing Sheets

OTHER PUBLICATIONS

K.L. Baumann et al., "The Convergent Synthesis of CI-981, an Optically Active, Highly Potent Tissue Selective Inhibitor of HMG-CoA Reductase," Tetrahedron Letters, vol. 33, No. 17 (1992) pp. 2283-2284.

Goodman and Gilman's The Pharmacological Basis of Therapeutics, 9th Ed. (1996) pp. 879-881.

Declaration Under Rule 132 by Thomas M. A. Bocan, dated Dec. 2, 1998, filed in U.S. Appl. No. 08/945,812; 2 pages.

Declaration Under Rule 132 by Stephen R. Bryn, dated Nov. 25, 1998, filed in U.S. Appl. No. 08/945,812; 3 pages.

Rouhi, Chem. & Eng. News, Feb. 24, 2003, pp. 32-35.

Cheronis, Semimicro Experimental Organic Chemistry, pp. 31-49, 1958.

Haleblian & Crone, 1969. J. Pharm. Sci.58:911-929.

David J. W. Grant, Theory and Origin of Polymorphisms, in Drugs of the Pharmaceutical Sciences, vol. 95, Polymorphism in Pharmaceutical Solids, Chapter 1, (Harry G. Brittain ed., 1999).

G. Michael Wall, "Pharmaceutical Applications of Drug Crystal Studies", Pharmaceutical Manufacturing (Feb. 1986) pp. 33-42.

U.S. Pharmacopia #23, p. 1843, 941 X-Ray Diffraction, 1995.

U.S. Appl. No. 10/994,142, Pending, filed Nov. 19, 2004, Aronhime et al.

McCrone W.C., "Polymorphism", Physics and Chemistry of the Organic Solid State, vol. 2, 1965, pp. 725-767.

Caira M.R., "Crystalline Polymorphisms of Organic Compounds" Topics in Current Chemistry, Springer, Berlin, DE, vol. 198, 1998, pp. 163-208.

Graul A., et al., "Atorvastatin Calcium" Drugs of the Future, Barcelona, ES, vol. 22, No. 9, 1997, pp. 956-968.

Guillory, J.K.: "in Polymorphism in Pharmaceutical Solids (Brittain, H.G., ed)", 1999, Marcel Dekker, Inc., New York, Basel, pp. 183-226.

Hancock B.C., et al., "Characteristics and Significance of the Amorphous State in Pharmaceutical Systems", Journal of Pharmaceutical Sciences, American Pharmaceutical Association, Washington, U.S., vol. 86, No. 1, Jan. 1997, pp. 1-12.

Concise Encyclopedia Chem. (1993), Walter deGruyter, Berlin, NY.

* cited by examiner

CRYSTAL FORMS OF ATORVASTATIN HEMI-CALCIUM AND PROCESSES FOR THEIR PREPARATION AS WELL AS NOVEL PROCESSES FOR PREPARING OTHER FORMS

CROSS-REFERENCE TO RELATED APPLICATIONS

This application is a divisional application of application Ser. No. 10/994,142, filed Nov. 19, 2004, now U.S. Pat. Ser. No. 7,144,916, which is a divisional application of application Ser. No. 09/997,126, filed Nov. 29, 2001, now abandoned, and claims the benefit of provisional applications Ser. Nos. 60/250,072, filed Nov. 30, 2000; 60/267,897, filed Feb. 9, 2001; 60/281,872, filed Apr. 5, 2001; 60/312,144, filed Aug. 13, 2001 and 60/326,529, filed Oct. 1, 2001, all of which are incorporated herein by reference.

FIELD OF THE INVENTION

The present invention relates to crystalline polymorphic forms of atorvastatin hemi-calcium, novel processes for preparing crystalline forms of atorvastatin hemi-calcium and crystalline atorvastatin hemi-calcium with a small particle size distribution

BACKGROUND OF THE INVENTION

Atorvastatin, ([R—(R*,R*)]-2-(4-fluorophenyl)-β,δ-dihydroxy-5-(1-methylethyl)-3-phenyl4-[(phenylamino)carbonyl]-1H-pyrrole-1-heptanoic acid), depicted in lactone form in formula (I) and its calcium salt trihydrate of formula (II) are well known in the art, and described, inter alia, in U.S. Pat. Nos. 4,681,893, 5,273,995, and in copending U.S. Ser. No. 60/166,153, filed Nov. 17, 2000, all of which are herein incorporated by reference.

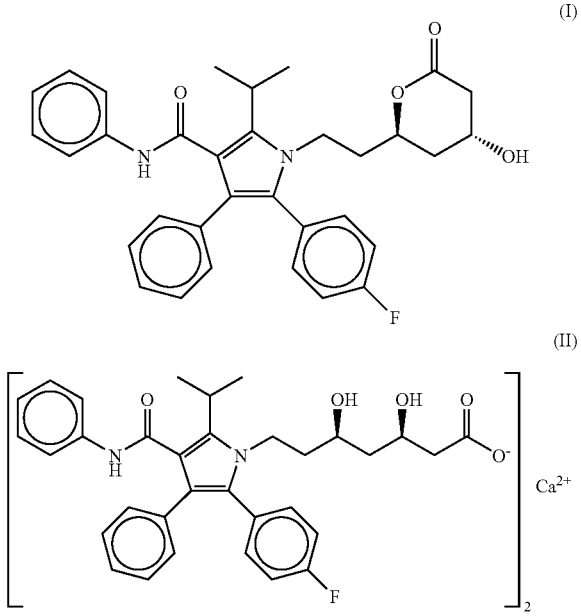

Atorvastatin is a member of the class of drugs called statins. Statin drugs are currently the most therapeutically effective drugs available for reducing low density lipoprotein (LDL) particle concentration in the blood stream of patients at risk for cardiovascular disease. A high level of LDL in the bloodstream has been linked to the formation of coronary lesions which obstruct the flow of blood and can rupture and promote thrombosis. Goodman and Gilman, *The Pharmacological Basis of Therapeutics* 879 (9th ed. 1996). Reducing plasma LDL levels has been shown to reduce the risk of clinical events in patients with cardiovascular disease and patients who are free of cardiovascular disease but who have hypercholesterolemia. Scandinavian Simvastatin Survival Study Group, 1994; Lipid Research Clinics Program, 1984a, 1984b.

The mechanism of action of statin drugs has been elucidated in some detail. They interfere with the synthesis of cholesterol and other sterols in the liver by competitively inhibiting the 3-hydroxy-3-methyl-glutaryl-coenzyme A reductase enzyme ("HMG-CoA reductase"). HMG-CoA reductase catalyzes the conversion HMG to mevalonate, which is the rate determining step in the biosynthesis of cholesterol, and so, its inhibition leads to a reduction in the concentration of cholesterol in the liver. Very low density lipoprotein (VLDL) is the biological vehicle for transporting cholesterol and triglycerides from the liver to peripheral cells. VLDL is catabolized in the peripheral cells which releases fatty acids which may be stored in adopcytes or oxidized by muscle. The VLDL is converted to intermediate density lipoprotein (IDL), which is either removed by an LDL receptor, or is converted to LDL. Decreased production of cholesterol leads to an increase in the number of LDL receptors and corresponding reduction in the production of LDL particles by metabolism of IDL.

Atorvastatin hemi-calcium salt trihydrate is marketed under the name LIPITOR by Warner-Lambert Co. Atorvastatin was first disclosed to the public and claimed in U.S. Pat. No. 4,681,893. The hemi-calcium salt depicted in formula (II) is disclosed in U.S. Pat. No. 5,273,995. The '995 patent teaches that the hemi-calcium salt is obtained by crystallization from a brine solution resulting from the transposition of the sodium salt with $CaCl_2$ and further purified by recrystallization from a 5:3 mixture of ethyl acetate and hexane.

The present invention provides new crystal forms of atorvastatin hemi-calcium in both solvated and hydrated states. The occurrence of different crystal forms (polymorphism) is a property of some molecules and molecular complexes. A single molecule, like the atorvastatin in formula (I) or the salt complex of formula (II), may give rise to a variety of solids having distinct physical properties like melting point, X-ray diffraction pattern, infrared absorption fingerprint and NMR spectrum. The differences in the physical properties of polymorphs result from the orientation and intermolecular interactions of adjacent molecules (complexes) in the bulk solid. Accordingly, polymorphs are distinct solids sharing the same molecular formula yet having distinct advantageous and/or disadvantageous physical properties compared to other forms in the polymorph family. One of the most important physical properties of pharmaceutical polymorphs is their solubility in aqueous solution, particularly their solubility in the gastric juices of a patient. For example, where absorption through the gastrointestinal tract is slow, it is often desirable for a drug that is unstable to conditions in the patient's stomach or intestine to dissolve slowly so that it does not accumulate in a deleterious environment. On the other hand, where the effectiveness of a drug correlates with peak bloodstream levels of the drug, a property shared by statin drugs, and provided the drug is rapidly absorbed by the GI system, then a more rapidly dissolving form is likely to exhibit increased effectiveness over a comparable amount of a more slowly dissolving form.

Crystalline Forms I, II, III and IV of atorvastatin hemi-calcium are the subjects of U.S. Pat. Nos. 5,959,156 and 6,121,461 assigned to Warner-Lambert and crystalline atorvastatin hemi-calcium Form V is disclosed in commonly-owned PCT Application No. PCT/US00/31555. There is an assertion in the '156 patent that Form I possesses more favorable filtration and drying characteristics than the known amorphous form of atorvastatin hemi-calcium. Although Form I remedies some of the deficiencies of the amorphous material in terms of manufacturability, there remains a need for yet further improvement in these properties as well as improvements in other properties such as flowability, vapor impermeability and solubility. Further, the discovery of new crystalline polymorphic forms of a drug enlarges the repertoire of materials that a formulation scientist has with which to design a pharmaceutical dosage form of a drug with a targeted release profile or other desired characteristic.

SUMMARY OF THE INVENTION

Figure 1:
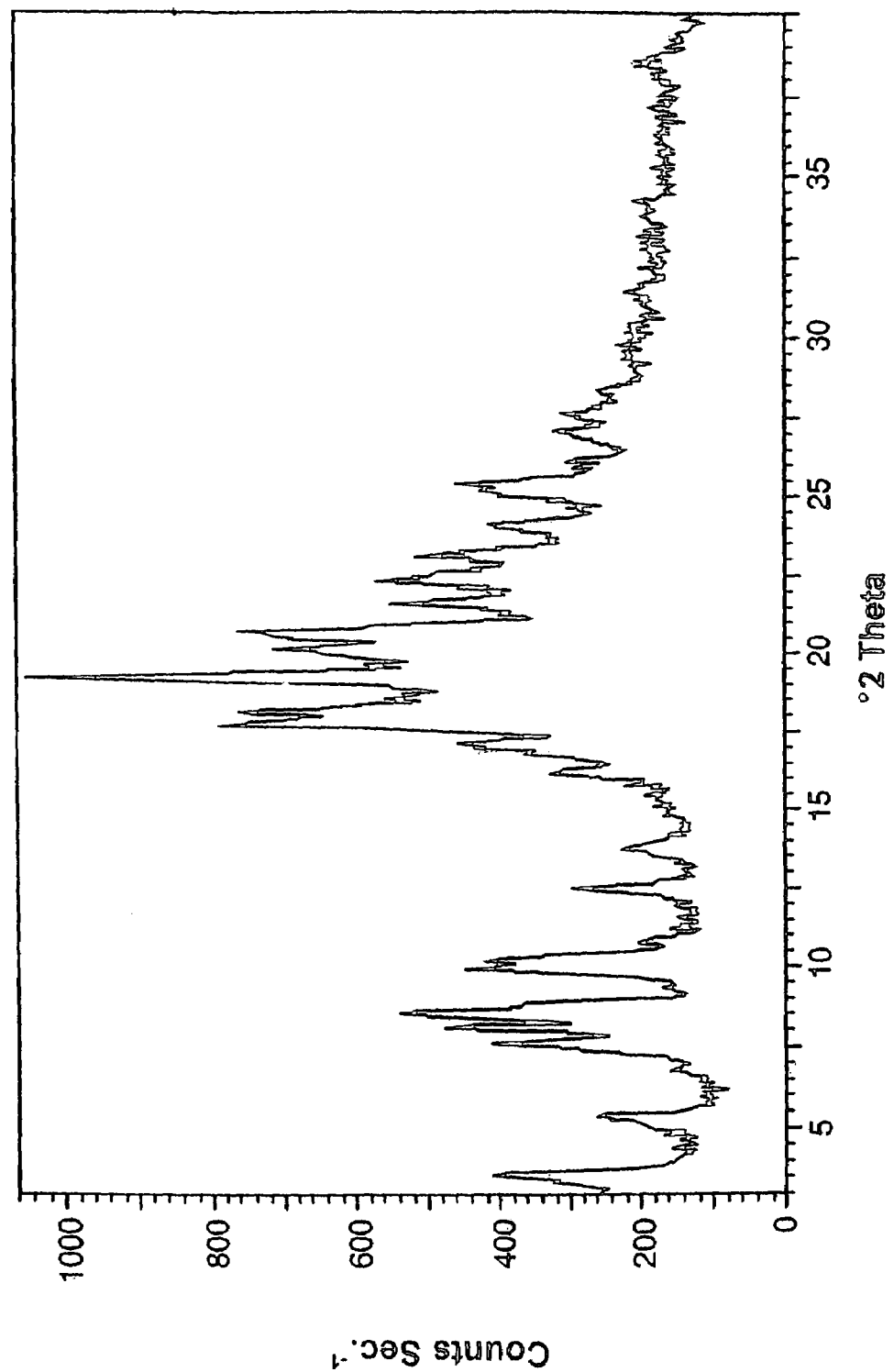
FIG. 1 is a characteristic powder X-ray diffraction pattern of atorvastatin hemi-calcium Form VI obtained using a conventional X-ray generator with a copper anode.

The present invention provides new atorvastatin hemi-calcium solvates and hydrates.

The present invention provides a novel crystalline form of atorvastatin hemi-calcium denominated Form VI and novel processes for its preparation.

In another aspect, the present invention provides a novel crystalline form of atorvastatin hemi-calcium denominated Form VIII and novel processes for its preparation.

In another aspect, the present invention provides a novel crystalline form of atorvastatin hemi-calcium denominated Form IX and novel processes for its preparation.

In another aspect, the present invention provides a novel crystalline form of atorvastatin hemi-calcium denominated Form X and novel processes for its preparation.

In another aspect, the present invention provides a novel crystalline form of atorvastatin hemi-calcium denominated Form XI and novel processes for its preparation.

In another aspect, the present invention provides a novel crystalline form of atorvastatin hemi-calcium denominated Form XII and novel processes for its preparation.

In another aspect, the present invention provides novel processes for preparing atorvastatin hemi-calcium Form I.

In another aspect, the present invention provides novel processes for preparing atorvastatin hemi-calcium Form II.

In another aspect, the present invention provides novel processes for preparing atorvastatin hemi-calcium Form IV.

In another aspect, the present invention provides novel processes for preparing atorvastatin hemi-calcium Form V.

In another aspect, the present invention provides novel processes for preparing amorphous atorvastatin hemi-calcium In another aspect, the invention provides compositions and dosage forms comprising atorvastatin hemi-calcium Forms VI, VII, VIII, IX, X, XI and their mixtures.

DETAILED DESCRIPTION OF THE PREFERRED EMBODIMENTS.

Some crystalline forms of atorvastatin hemi-calcium of the present invention exist in a solvated state and hydrated state. Hydrates have been analyzed by Karl-Fisher and thermogravimetric analysis.

Powder X-ray diffraction ("PXRD") analysis employing conventional CuK$_\alpha$ radiation was performed by methods known in the art using a SCINTAG powder X-ray diffractometer model X'TRA equipped with a solid-state detector. Copper radiation of $\lambda$=1.5418 Å was used. Measurement range: 2-40 degrees 2θ. The sample was introduced using a round standard aluminum sample holder with round zero background quartz plate in the bottom. Powdered samples were gently ground and filled in the round cavity of the sample holder by pressing with a glass plate.

PXRD analysis using a synchrotron X-ray source was performed at the National Synchrotron Light Source of the Brookhaven National Laboratory (diffractometer station X3B1). Samples were loosely packed into thin-walled glass capillaries. X-ray radiation was approximately 1.15 Å. Since the wavelength of incident light does correspond to the wavelength most commonly used in conventional PXRD analysis, X-ray peak positions in the diffraction patterns obtained from the synchrotron source are expressed in terms of d spacings, which are invariant with changes in wavelength of the X-radiation used to produce the pattern. The scan width was from 1 to 20 degrees 2θ. The resolution of the spectra is in the range of 0.01 to 0.03 degrees full width at half maximum. The positions of well resolved peaks are accurate to within 0.003 to 0.01 degrees.

The CP/MAS $^{13}$C NMR measurements were made at 125.76 MHz and were performed on a Bruker DMX-500 digital FT NMR spectrometer equipped with a BL-4 CP/MAS probehead and a High Resolution/High Performance $^1$H preamplifier for solids: spin rate 5.0 kHz, pulse sequence SELTICS, sample holder: Zirconia rotor 4 mm diameter.

Atorvastatin hemi-calcium Form VI is characterized by a powder X-ray diffraction pattern (FIG. 1) with peaks at 3.5, 5.1, 7.7, 8.2, 8.7, 10.0, 12.5, 13.8, 16.2, 17.2, 17.9 18.3, 19.5, 20.4, 20.9, 21.7, 22.4, 23.2, 24.3, 25.5±0.2 degrees two-theta. The most characteristic peak is observed at 19.5±0.2 degrees two-theta. The PXRD pattern of Form VI was taken using a Phylips diffractometer similar to the SCINTAG instrumentation described above.

Atorvastatin hemi-calcium Form VI may be obtained by dissolving any other form of atorvastatin hemi-calcium, preferably Form I in acetone and then precipitating Form VI by addition of an anti-solvent, preferably water.

Figure 2:
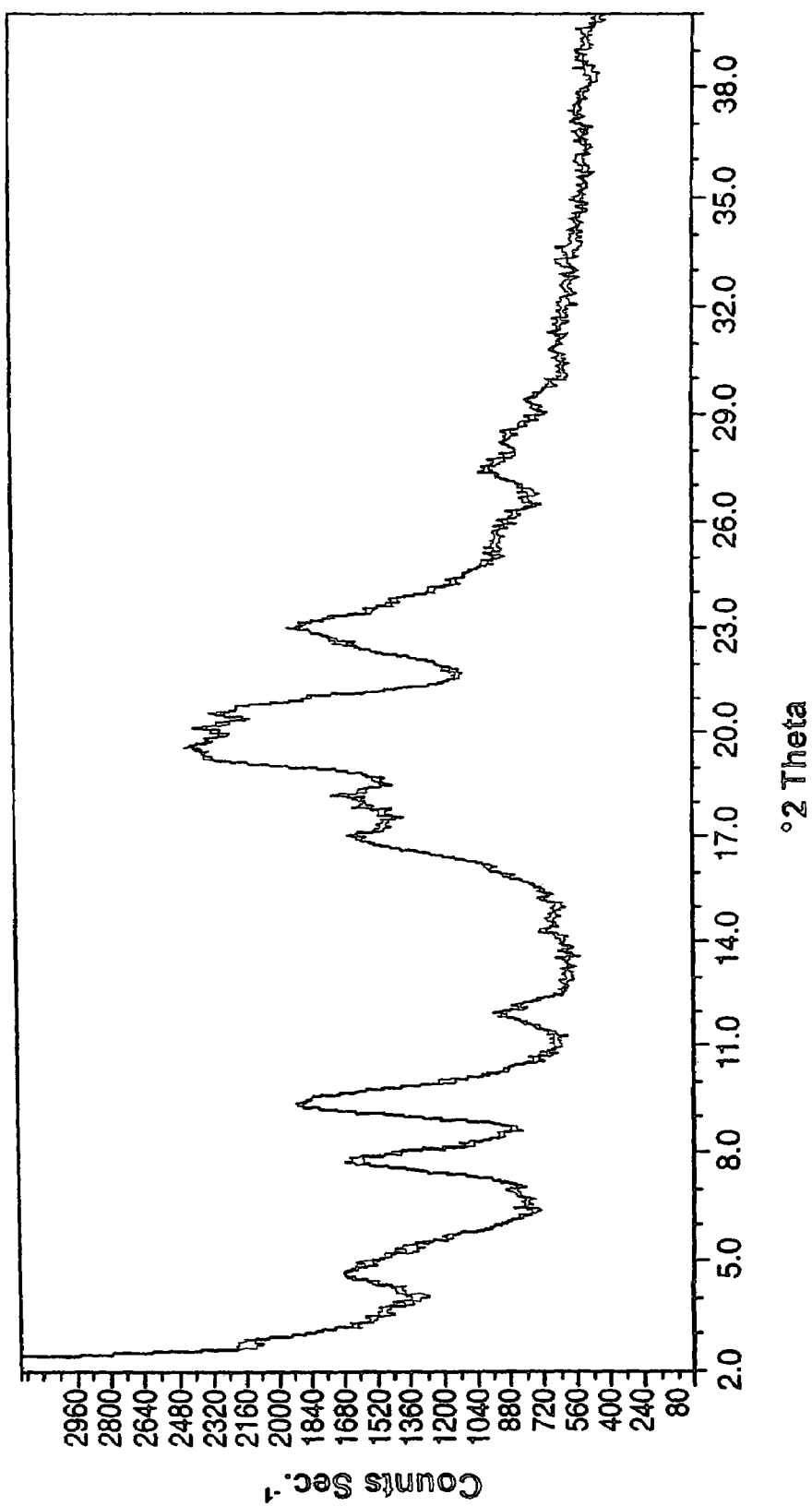
FIG. 2 is a characteristic powder X-ray diffraction pattern of atorvastatin hemi-calcium Form VII obtained using a conventional X-ray generator with a copper anode.

Atorvastatin hemi-calcium Form VII is characterized by a powder X-ray diffraction pattern (FIG. 2) having two broad peaks, one in the range 18.5-21.8 and the other in the range of 21.8-25.0 degrees 2θ, and other additional broad peaks at 4.7, 7.8, 9.3, 12.0, 17.1, 18.2±0.2 degrees 2θ. Samples of Form VII may contain up to 12% water.

Form VII is readily distinguished from known forms of atorvastatin hemi-calcium by the broad peaks at 7.8 and 9.3±0.2 degrees 2θ. For instance, Form I has peaks at 9.2, 9.5, 10.3, 10.6, 11.0 and 12.2 degrees 2θ according to the information provided in U.S. Pat. No. 5,969,156. In this region, Form II has two sharp peaks at 8.5 and 9.0 degrees 2θ and Form IV has one strong peak at 8.0 degrees 2θ. The other broad peaks in the region of 15-25 degrees 2θ distinguish Form VII from all other forms. Forms I, III and IV all have sharp peaks in this region.

Atorvastatin hemi-calcium Form VII may be prepared by treating atorvastatin calcium Forms I or V with ethanol, preferably absolute ethanol, at room temperature to reflux temperature for a period of from about 1 h to about 24 h, preferably 2.5-16 h. If the process is carried out in refluxing EtOH, the conversion is complete in about 2.5 h. If the process is carried out at room temperature a longer period is required.

Figure 3:
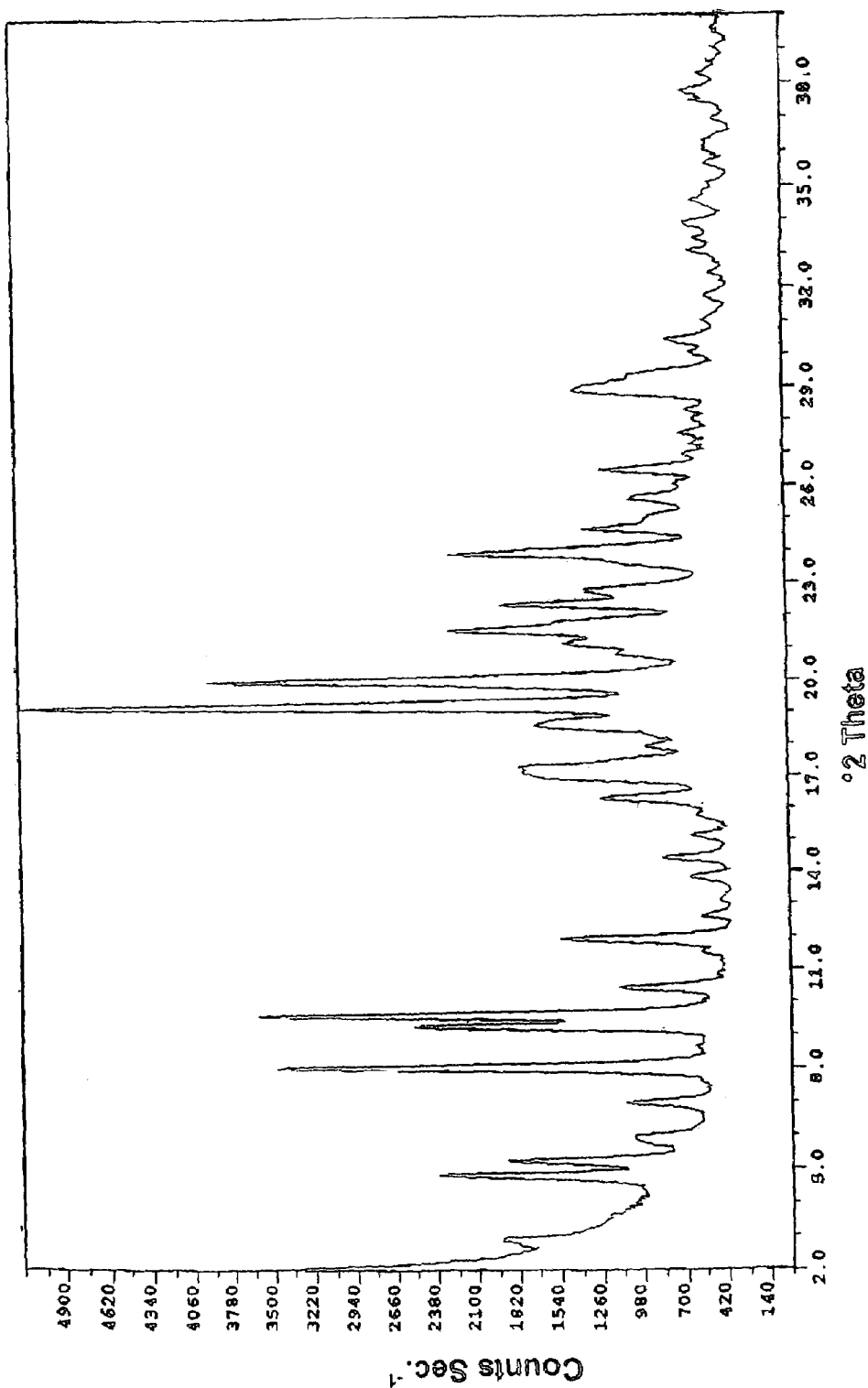
FIG. 3 is a characteristic powder X-ray diffraction pattern of atorvastatin hemi-calcium Form VIII obtained using a conventional X-ray generator with a copper anode.

Atorvastatin hemi-calcium Form VIII is characterized by a powder X-ray diffraction pattern (FIG. 3) obtained using conventional CuK$_\alpha$ radiation having peaks at 4.8, 5.2, 5.9, 7.0, 8.0, 9.3, 9.6, 10.4, 11.9, 16.3, 17.1(broad), 17.9, 18.6, 19.2, 20.0, 20.8, 21.1, 21.6, 22.4, 22.8, 23.9, 24.7, 25.6, 26.5, 29.0±0.2 degrees two-theta. The most characteristic peaks are at 6.9, 9.3, 9.6, 16.3, 17.1, 19.2, 20.0, 21.6, 22.4, 23,9, 24.7, 25.6, and 26.5±0.2 degrees 2θ. Samples of atorvastatin hemi-calcium Form VIII were found to contain up to 7% water by Karl Fisher. Form VIII is readily distinguished from Forms I-IV by its characteristic sharp peaks at 9.3 and 9.6 degrees 2θ. According to the information provided in U.S. Pat. No. 5,969,156, Form I has one medium peak at 6.9 and sharp peaks at 9.2, 9.5, 10.3, 10.6, 11.0 and 12.2±0.2 degrees 2θ. Form IV is said to have two peaks at 8.0 and 9.7 degrees 2θ. Form II is said to have in this region two sharp peaks at 8.5 and 9.0 degrees 2θ. Form III has in this region one strong sharp peak at 8.7 degrees 2θ according to the information provided in U.S. Pat. No. 6,121,461. The features are not observed in the Form VIII PXRD pattern. Further, there is in the PXRD pattern of Form VIII one sharp, medium intensity peak at 7.0 which is well distinguished from other peaks in the region. A comparison of the PXRD pattern of Form VIII with the patterns of Forms I-IV reveals that this feature of the Form VIII pattern is distinctive.

Other peaks in the Form VIII pattern that are unique to this form are the two strong and sharp peaks at 19.2 and 20.0 degrees 2θ. In this region, Form I has sharp peaks at 21.6, 22.7, 23.3 and 23.7 degrees 2θ according to the information provided in the '156 patent. Form IV is said to have peaks at 18.4 and 19.6 degrees 2θ, while Form I has two main peaks at 17.0 and 20.5 and Form III has peaks at 17.7, 18.2, 18.9, 20.0 and 20.3±0.2 degrees 2θ.

Synchrotron X-ray powder diffraction analysis was performed on Form VIII to determine its crystal system and unit cell dimensions. Form VIII has a monoclinic unit cell with lattice dimensions: a=18.55-18.7 Å, b=5.52-5.53 Å, c=31.0-31.2 Å and angle β between the a and c axes of 97.5-99.5°. The unit cell parameters were determined using the Le Bail method.

Figure 4:
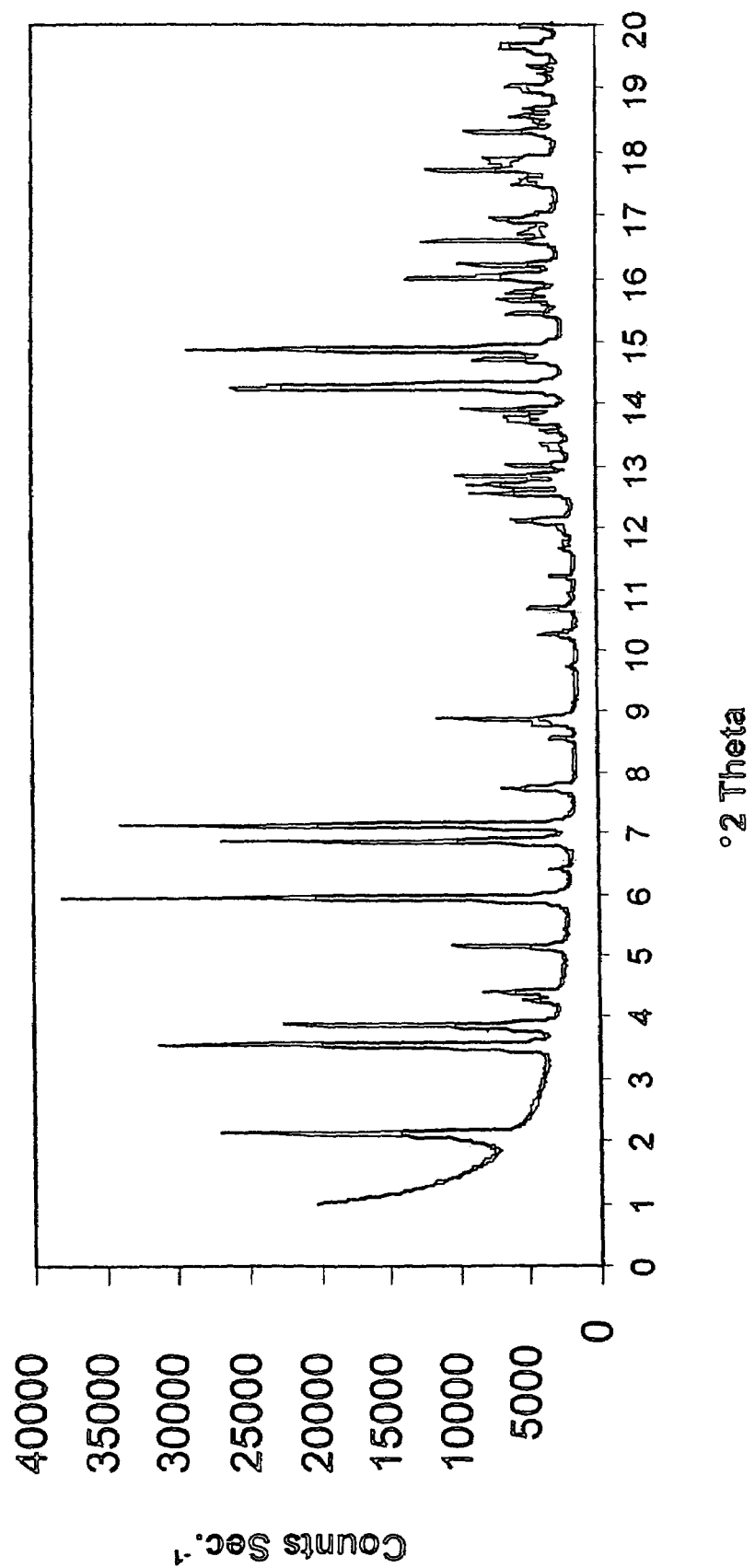
FIG. 4 is a characteristic powder X-ray diffraction pattern of atorvastatin hemi-calcium Form VIII obtained using a synchrotron X-ray source.

The diffractogram of FIG. 4 obtained using a synchrotron X-ray source has many sharp well resolved peaks. The d-spacings of some of the more prominent peaks are listed in Table 1, along with the positions in units of two-theta that the peaks would have using CuK radiation of 1.541.8Å.

TABLE 1

| d (Å) | 2θ[a] |
|---|---|
| 30.81 | 2.87 |
| 18.46 | 4.79 |
| 16.96 | 5.21 |
| 15.39 | 5.74 |
| 14.90 | 5.93 |
| 12.78 | 6.92 |
| 11.05 | 8.00 |
| 9.58 | 9.23 |
| 9.22 | 9.59 |
| 7.42 | 11.93 |
| 6.15 | 14.40 |
| 5.43 | 16.32 |
| 4.62 | 19.21 |
| 4.44 | 20.00 |
| 3.98 | 22.34 |

[a]Calculated from d for CuK$_\alpha$ radiation

Because of the natural variation between independent samples and measurements, the peak positions may deviate from the reported positions by as much as 0.5% of the d values. There may be larger shifts if the material undergoes size reduction a as micronization.

Figure 5:
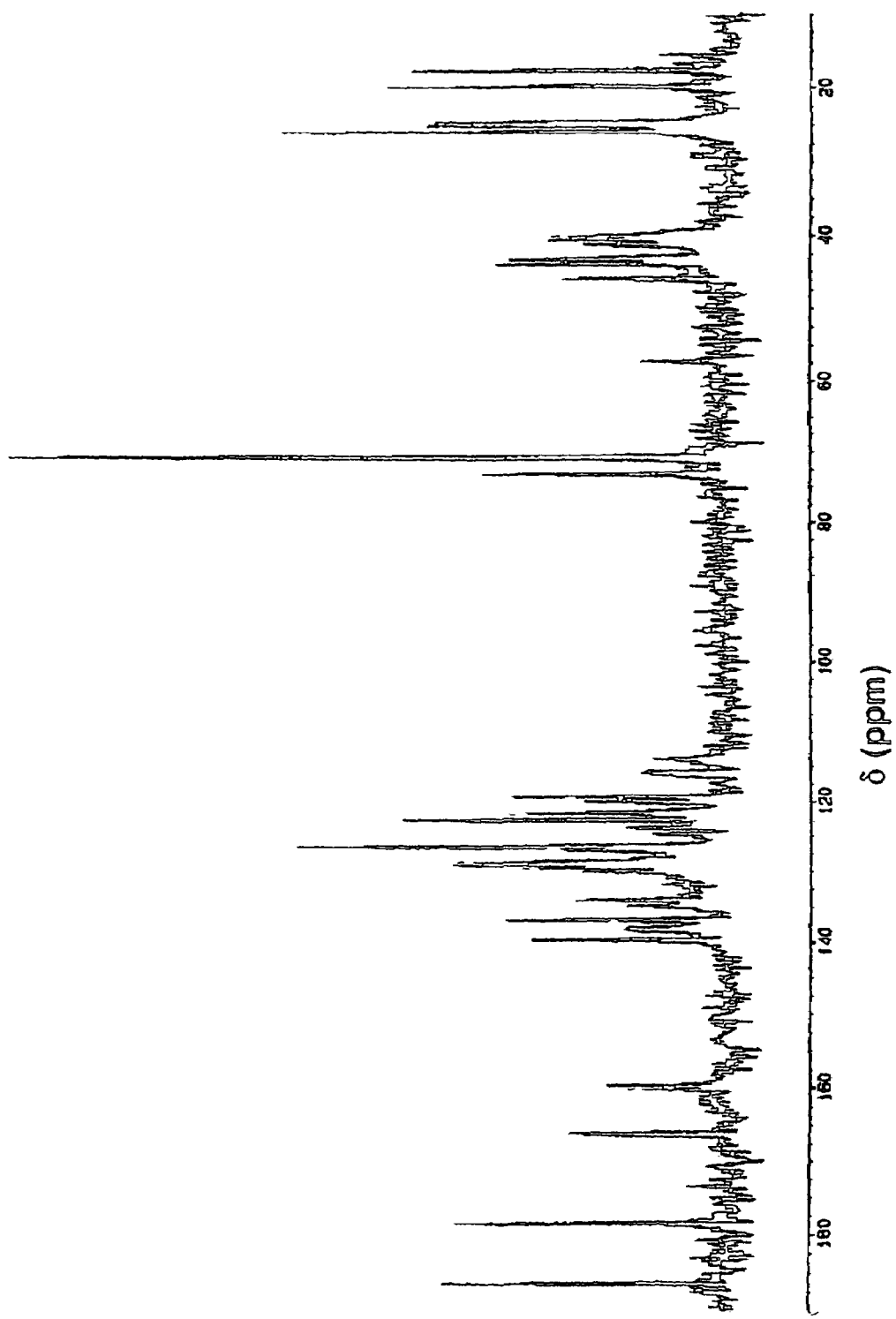
FIG. 5 is a characteristic solid state $^{13}$C NMR spectrum of atorvastatin Form VIII.
Figure 6:
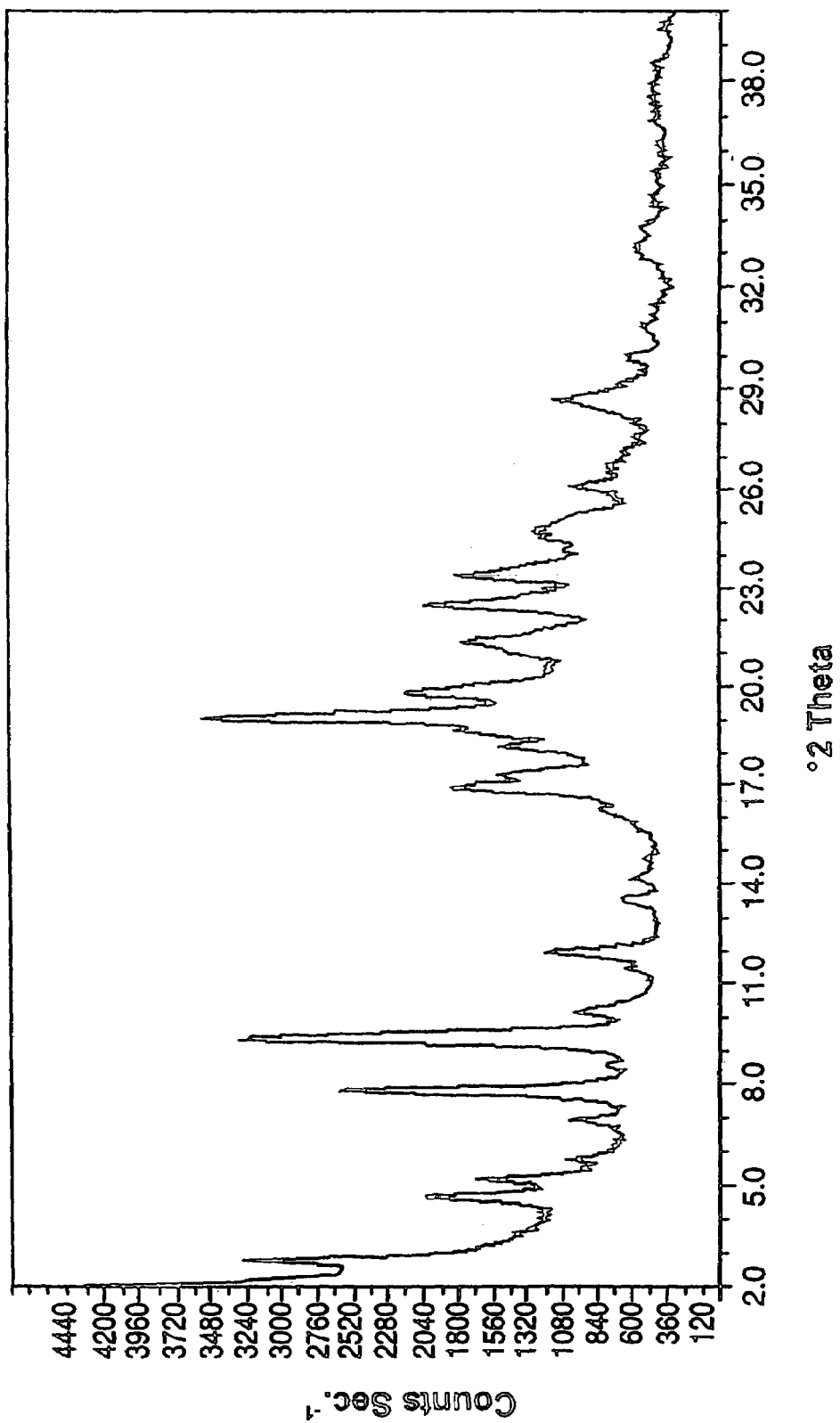
FIG. 6 is a characteristic powder X-ray diffraction pattern of atorvastatin hemi-calcium Form IX obtained using a conventional X-ray generator with a copper anode.

Atorvastatin hemi-calcium Form VIII produced the solid-state $^{13}$C NMR spectrum shown in FIG. 5. Form VIII is characterized by the following solid-state. $^{13}$C nuclear magnetic resonance chemical shifts in ppm: 17.8, 20.0, 24.8, 25.2, 26.1, 40.3, 40.8, 41.5, 43.4, 44.1, 46.1, 70.8, 73.3, 114.1, 116.0, 119.5, 120.1, 121.8, 122.8, 126.6, 128.8, 129.2, 134.2, 135.1, 137.0, 138.3, 139.8, 159.8, 166.4, 178.8, 186.5. Form VIII is characterized by a solid-state $^{13}$C nuclear magnetic resonance having the following chemical shifts differences between the lowest ppm resonance and other resonances: 2.2, 7.0, 7.4, 8.3, 22.5, 23.0, 23.7, 25.6, 26.3, 28.3, 53.0, 55.5, 96.3, 98.2, 101.7, 102.3, 104.0, 105.0, 108.8, 111.0, 111.4, 116.4, 117.3, 119.2, 120.5, 122.0, 142.0, 148.6, 161.0 and 168.7. The chemical shifts reported for Form VIII are averaged from spectra taken of four samples of Form VIII. Characteristic parts of the pattern are found at 24-26 ppm (aliphatic range), 119-140 ppm (aromatic range) and other regions. The shift values are accurate to within ±0.1 ppm, except for the carbonyl peak at 178.8 ppm which has a fluctuation of ±0.4ppm.

Atorvastatin hemi-calcium Form VIII can exist as an ethanol solvate containing up to about 3% ethanol by weight.

The following methods have been found suitable for generating Form VIII. This form may, however, also be accessible by empirical development and by routine modification of these procedures.

Atorvastatin hemi-calcium Form VIII may be obtained by slurrying atorvastatin hemi-calcium in a mixture of ethanol and water at elevated temperature, preferably about 78-80° C. The slurrying procedure may be incorporated into the last step of a process for preparing atorvastatin hemi-calcium, which typically is generation of the hemi-calcium salt from the atorvastatin free acid or lactone by treatment with a source of calcium ion. In such a combined procedure the salt is generated in a solvent system comprising ethanol and water. Conveniently, after precipitation of the atorvastatin hemi-calcium salt by an additional amount of water, the salt may be slurried in the reaction mixture for a period of several hours, preferably from about 6 to about 16 hours to obtain atorvastatin hemi-calcium Form VIII.

Form VIII also may be obtained starting from Form V by treating Form V with a mixture of EtOH:$H_2O$, preferably in the ratio of about 5:1 at an elevated temperature below reflux, preferably 78-80° C. An especially preferred EtOH:$H_2O$ mixture contains about 4% by volume water in ethanol. During the heating, atorvastatin Form V gradually dissolves and at the point of 78-80° C. turbidity, with or without seeding, is observed. At this point the suspension is immediately cooled to room temperature.

Form VIII may be obtained by treating atorvastatin hemi-calcium in EtOH, preferably absolute EtOH, at elevated temperature, preferably boiling EtOH. Under these conditions, the atorvastatin dissolves and reprecipitates. MeOH may be added at reflux. Added MeOH may adversely affect the yield, but may improve the chemical purity of the product. Starting materials for preparing Form VIII by this process can be crystalline forms of atorvastatin hemi-calcium, preferably Forms I and V and mixtures thereof or amorphous atorvastatin hemi-calcium.

The quantity of EtOH or mixture thereof with water is preferably in the range of from about 10 to about 100 ml $g^{-1}$, more preferably about 20 to about 80 ml $g^{-1}$.

We have discovered that atorvastatin hemi-calcium that contains greater than 0.1% des-fluoro atorvastatin hemi-calcium and/or greater than 1% trans atorvastatin hemi-calcium may be purified by suspending in a solution of about 96% ethanol and about 4% water at elevated temperature, preferably at reflux temperature. Typically, atorvastatin hemi-calcium is recovered with less than 0.07% contamination with des-fluoro atorvastatin hemi-calcium and less than 0.6% contamination with trans atorvastatin hemi-calcium.

Form VIII also may be prepared by suspending atorvastatin hemi-calcium in certain 1-butanol/water and ethanol/water mixtures for a period of time sufficient to cause the conversion of the atorvastatin hemi-calcium to Form VIII. 1-Butanol/water mixtures should contain about 20% 1-butanol by volume at elevated temperature, preferably at reflux temperature.

Atorvastatin hemi-calcium Form IX is characterized by a powder X-ray diffraction pattern (FIG. 5) with peaks at 4.7, 5.2, 5.7, 7.0, 7.9, 9.4, 10.2, 12.0, 17.0, 17.4, 18.2, 19.1, 19.9, 21.4, 22.5, 23.5, 24.8 (broad), 26.1, 28.7, 30.0±0.2 degrees two-theta. The most characteristic peaks of Form IX are at 6.9, 17.0, 17.4, 18.2, 18.6, 19.1, 19.9, 21.4, 22.5 and 23.5±0.2 degrees two-theta. Form IX may contain up to 7% water. Form IX also can exist as a butanol solvate containing up to about 5% butanol.

Form IX is readily distinguished by its characteristic sharp peaks at 18.6, 19.1, 19.9, 21.4, 22.5, 23.5 degrees 2θ. For comparison, Form I has sharp peaks at 21.6, 22.7, 23.3 and 23.7 degrees 2θ, while Form IV has in this region sharp peaks at 18.4, and 19.6 degrees 2θ and Form II has two main peaks at 17.0 and 20.5 degrees 2θ, according to information in the '156 patent. Form III has in this region peaks at 17.7, 18.3, 18.9, 20.0 and 20.3 degrees 2θ. Also, there is in the PXRD pattern of Form IX, as there is in the pattern of Form VIII, a sharp, well distinguished medium intensity peak at 7.0 degrees 2θ.

The crystal system and unit cell dimension of Form IX were determined using synchrotron X-ray powder diffraction analysis. Form IX has a monoclinic crystal lattice with lattice dimensions: a=18.75-18.85 Å, b=5.525-5.54 Å, c=30.9-31.15 Å and angle β between the a and c axes of 96.5-97.5°.

Figure 7:
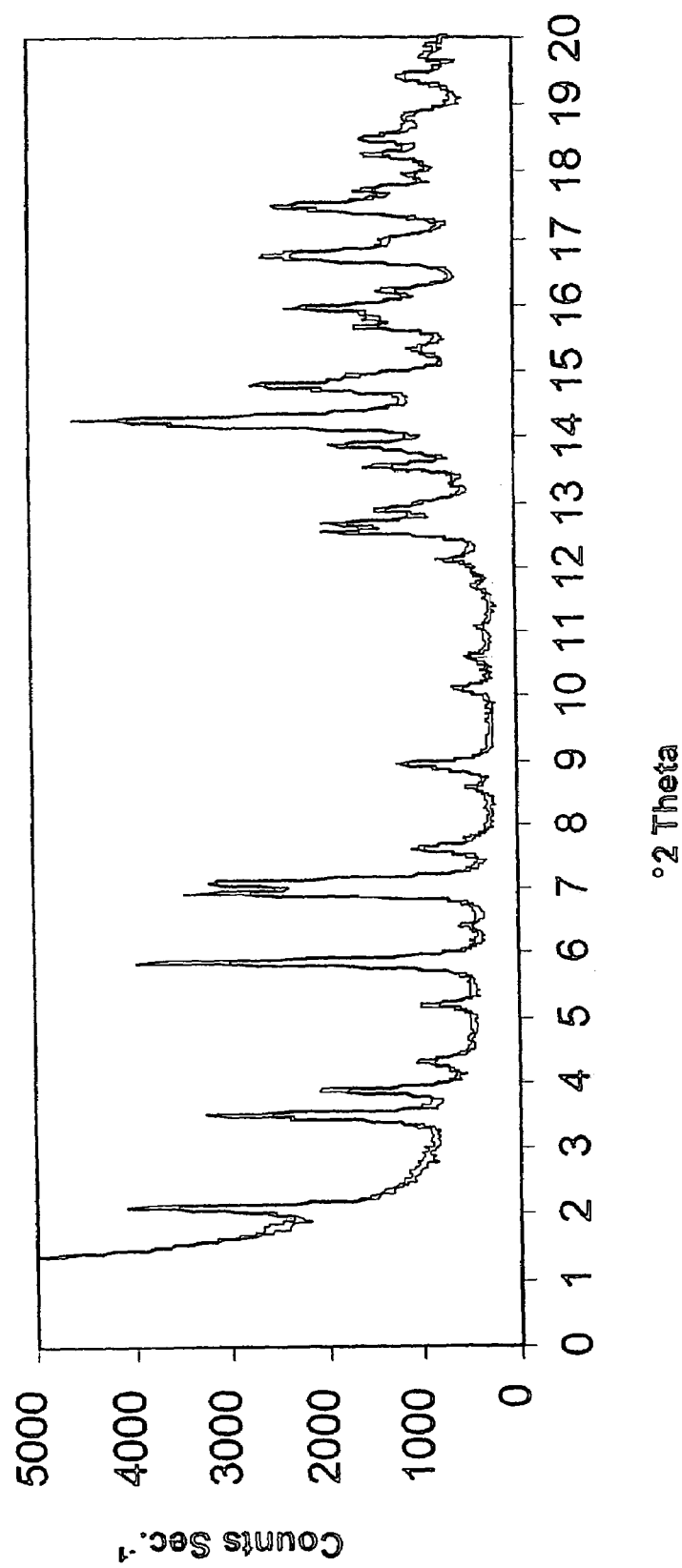
FIG. 7 is a characteristic powder X-ray diffraction pattern of atorvastatin hemi-calcium Form IX obtained using a synchrotron X-ray source.

The d-spacings of some of the more prominent peaks in the synchrotron X-ray powder diffractogram of FIG. 7 are listed in Table 2, along with the positions in units of two-theta that the peaks would have using $CuK_\alpha$ radiation.

TABLE 2

| d (Å) | 2θ[a] |
|---|---|
| 30.86 | 2.86 |
| 18.67 | 4.73 |
| 16.91 | 5.23 |
| 15.17 | 5.83 |
| 12.66 | 6.98 |
| 11.20 | 7.89 |
| 9.50 | 9.31 |
| 9.28 | 9.53 |
| 8.63 | 10.25 |
| 7.69 | 11.51 |
| 7.38 | 11.99 |
| 6.51 | 13.60 |
| 5.45 | 16.26 |
| 5.26 | 16.86 |
| 5.20 | 17.05 |
| 5.12 | 17.32 |
| 4.87 | 18.22 |
| 4.76 | 18.64 |
| 4.63 | 19.17 |
| 4.47 | 19.86 |
| 4.14 | 21.46 |
| 4.08 | 21.78 |
| 3.78 | 23.54 |
| 3.73 | 23.86 |
| 3.62 | 24.59 |
| 3.58 | 24.87 |

[a]Calculated from d for $CuK_\alpha$ radiation

Because of the natural variation between independent samples and measurements, the peak positions may deviate from the reported positions by as much as 0.5% of the d values. There may be larger shifts if the material undergoes size reduction as micronization.

Figure 8:
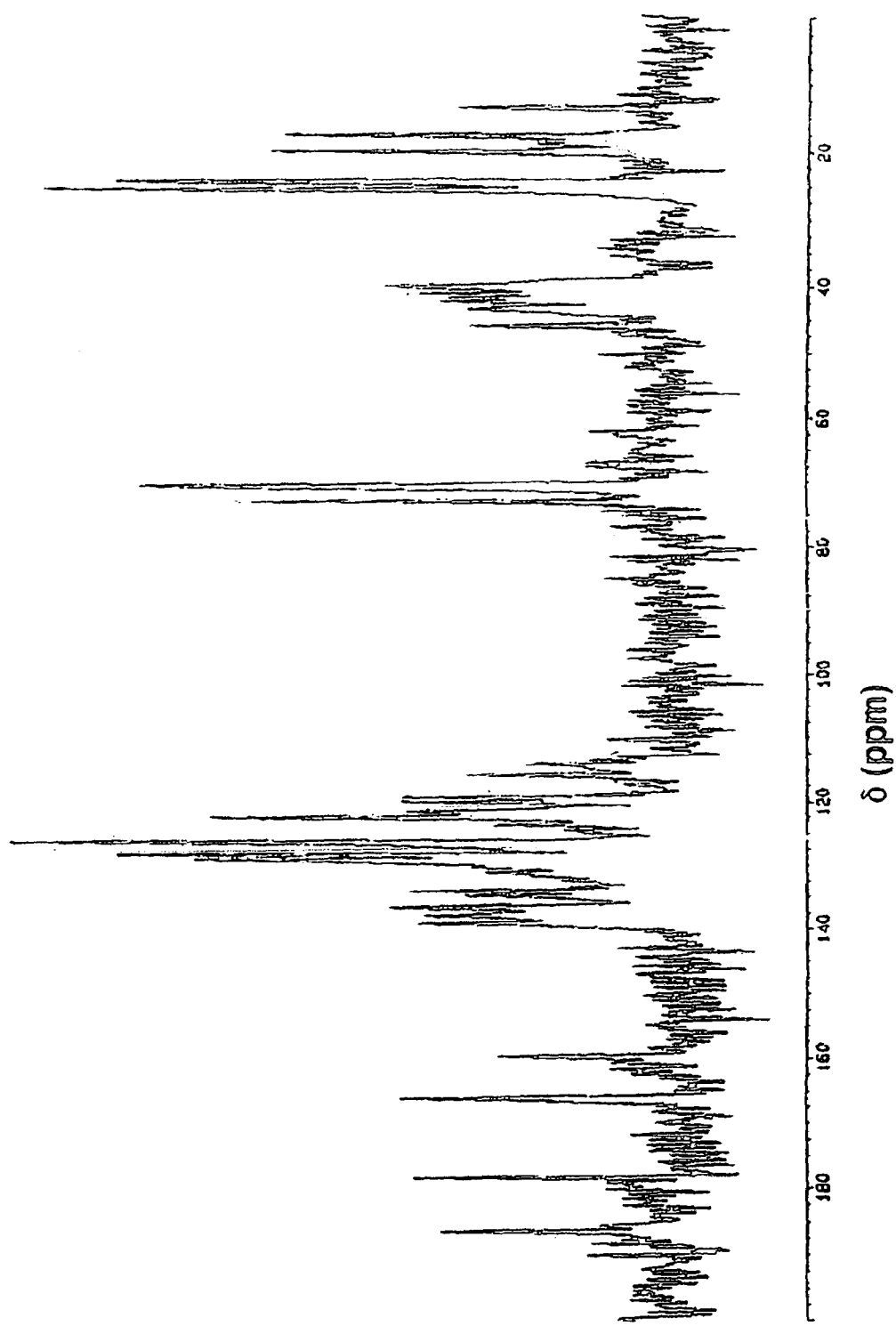
FIG. 8 is a characteristic solid state $^{13}$C NMR spectrum of atorvastatin Form IX.

Atorvastatin hemi-calcium Form IX produced the solid-state $^{13}C$ NMR spectrum shown in FIG. 8. Form IX is characterized by the following solid-state $^{13}C$ nuclear resonance chemical shifts in ppm: 18.0, 20.4, 24.9, 26.1, 40.4, 46.4, 71.0, 73.4, 114.3, 116.0, 119.5, 120.2, 121.7, 122.8, 126.7, 128.6, 129.4, 134.3, 135.1, 136.8, 138.3, 139.4, 159.9, 166.3, 178.4, 186.6. Form IX is characterized by a solid-state $^{13}C$ nuclear resonance having the following chemical shifts differences between the lowest ppm resonance and other resonances: 2.4, 6.9, 8.1, 22.4, 28.4, 53.0, 55.4, 96.3, 98.0, 101.5, 102.2, 103.7, 104.8, 108.7, 110.6, 111.4, 116.3, 117.1, 118.8, 120.3, 121.4, 141.9, 148.3, 160.4, 168.6. Characteristic parts of the pattern are found at 24-26 ppm (aliphatic range), 119-140 ppm (aromatic range) and other regions. The chemical shifts of Form IX are an average taken from spectra on two samples of Form IX. The shift values are accurate to within ±0.1 ppm.

Form IX may be prepared by the following processes though this form may be accessed by empirical development and by routine modification of these procedures.

Atorvastatin hemi-calcium Form IX may be prepared by slurrying atorvastatin hemi-calcium in butanol and isolating Form IX by, for example, filtration or decantation of the butanol, preferably by filtration. Preferred temperature ranges for the slurrying are from 78° C. to the reflux temperature of the solvent. Recovery of atorvastatin hemi-calcium salt from the slurry can be enhanced by addition of an anti-solvent to the slurry before isolating Form IX. Preferred anti-solvents include isopropanol and n-hexane. Starting materials for preparing Form IX by this process can be crystalline or amorphous atorvastatin hemi-calcium, preferably Forms I and V and mixtures thereof.

Form IX may be prepared by suspending Form VIII in ethanol, preferably absolute ethanol, at room temperature for a period of time sufficient to convert form VIII to Form IX, which may range from a few hours to 24 hours and typically requires about 16. hours. Thereafter Form IX is recovered from the suspension. Form IX also may be prepared by maintaining Form VIII under a humid atmosphere.

Form IX also may be prepared by suspending atorvastatin hemi-calcium Form V in mixtures of 1-butanol and either ethanol or water at reflux temperature for a period of time sufficient to convert Form V into Form IX and recovering Form IX from the suspension. Preferably the mixtures contain about 50 volume percent of each component.

Atorvastatin hemi-calcium Form X is characterized by a powder X-ray diffraction pattern (FIG. 7) having peaks at 4.8, 5.3, 5.9, 9.6, 10.3, 11.5, 12.0, a double peak at 16.1 and 16.3, 16.9, 17.4, 18.2, 19.2, 19.4, 20.0, 20.8, 21.6, 22.0, 22.8, 23.6, 24.6, 25.0, 25.5, 26.2, 26.8, 27.4, 28.0, 30.3±0.2 degrees 2θ. The most characteristic peaks are two peaks at 20.0 and 20.8±0.2 degrees 2θ and other peaks at 19.1, 19.4, 22.8, 23.6, 25.0, 28.0, 30.3±0.2 degrees 2θ. Form X contains up to 2% ethanol and may contain up to 4% water.

Form X is distinguished from that of Form IV by having characteristic peaks at 7.0, 19.9, 20.7, 24.1, 25.0, 28.0 and 30.3±0.2 degrees 2θ. These features are clearly distinguished from those appearing the corresponding regions of the PXRD patterns of Forms I-IV which have been previously described.

The crystal system and unit cell dimension of Form X were determined using synchrotron X-ray powder diffraction analysis. Form X has a monoclinic crystal lattice with lattice dimensions: a=18.55-18.65 Å, b=5.52-5.53 Å, c=30.7-30.85 Å and angle β between the a and c axes of 95.7-96.7°.

Figure 10:
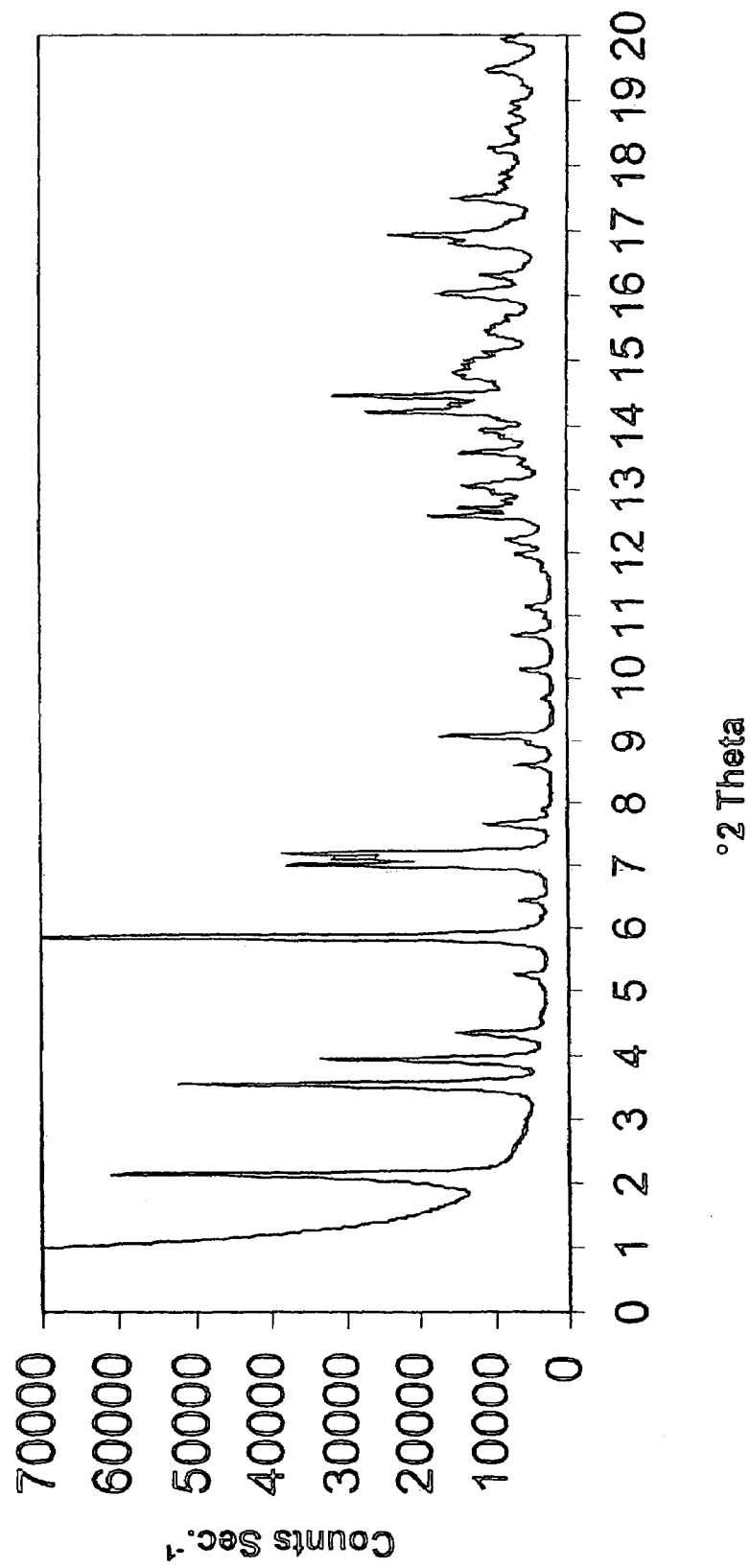
FIG. 10 is a characteristic powder X-ray diffraction pattern of atorvastatin hemi-calcium Form X obtained using a synchrotron X-ray source.

The d-spacings of some of the more prominent peaks in the synchrotron X-ray powder diffractogram of FIG. 10 are listed in Table 3, along with the positions in units of two-theta that the peaks would have using $CuK_\alpha$ radiation.

TABLE 3

| d (Å) | 2θ[a] |
|---|---|
| 30.63 | 2.88 |
| 18.49 | 4.78 |
| 16.66 | 5.30 |
| 15.12 | 5.85 |
| 12.49 | 7.08 |
| 11.19 | 7.90 |
| 10.20 | 8.67 |
| 9.38 | 9.43 |
| 9.24 | 9.57 |
| 9.13 | 9.69 |
| 8.58 | 10.31 |
| 7.64 | 11.58 |
| 7.36 | 12.02 |
| 7.26 | 12.19 |
| 6.81 | 13.00 |
| 6.50 | 13.62 |
| 6.16 | 14.38 |
| 5.91 | 14.99 |
| 5.24 | 16.92 |

TABLE 3-continued

| d (Å) | 2θ[a] |
|---|---|
| 5.19 | 17.08 |
| 5.06 | 17.53 |
| 4.86 | 18.25 |
| 4.74 | 18.72 |
| 4.65 | 19.09 |
| 4.61 | 19.25 |
| 4.56 | 19.47 |
| 4.12 | 21.57 |
| 4.10 | 21.95 |
| 3.93 | 22.62 |
| 3.90 | 22.80 |
| 3.77 | 23.60 |

[a]Calculated from d for $CuK_\alpha$ radiation

Because of the natural variation between independent samples and measurements, the peak positions may deviate from the reported positions by as much as 0.5%. There may be larger shifts if the material undergoes size reduction as micronization.

Figure 11:
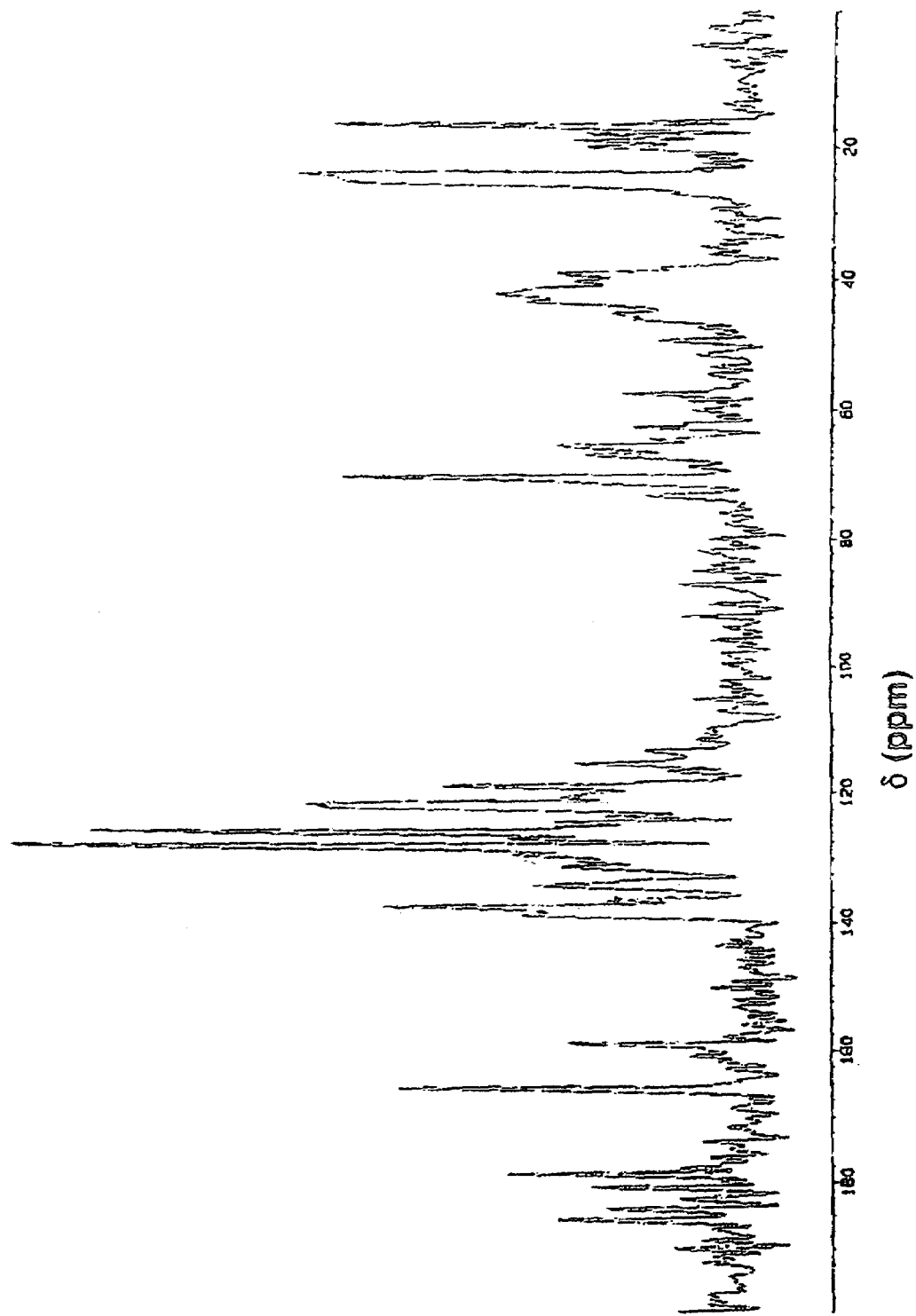
FIG. 11 is a characteristic solid state $^{13}$C NMR spectrum of atorvastatin hemi-calcium Form X.
Figure 12:
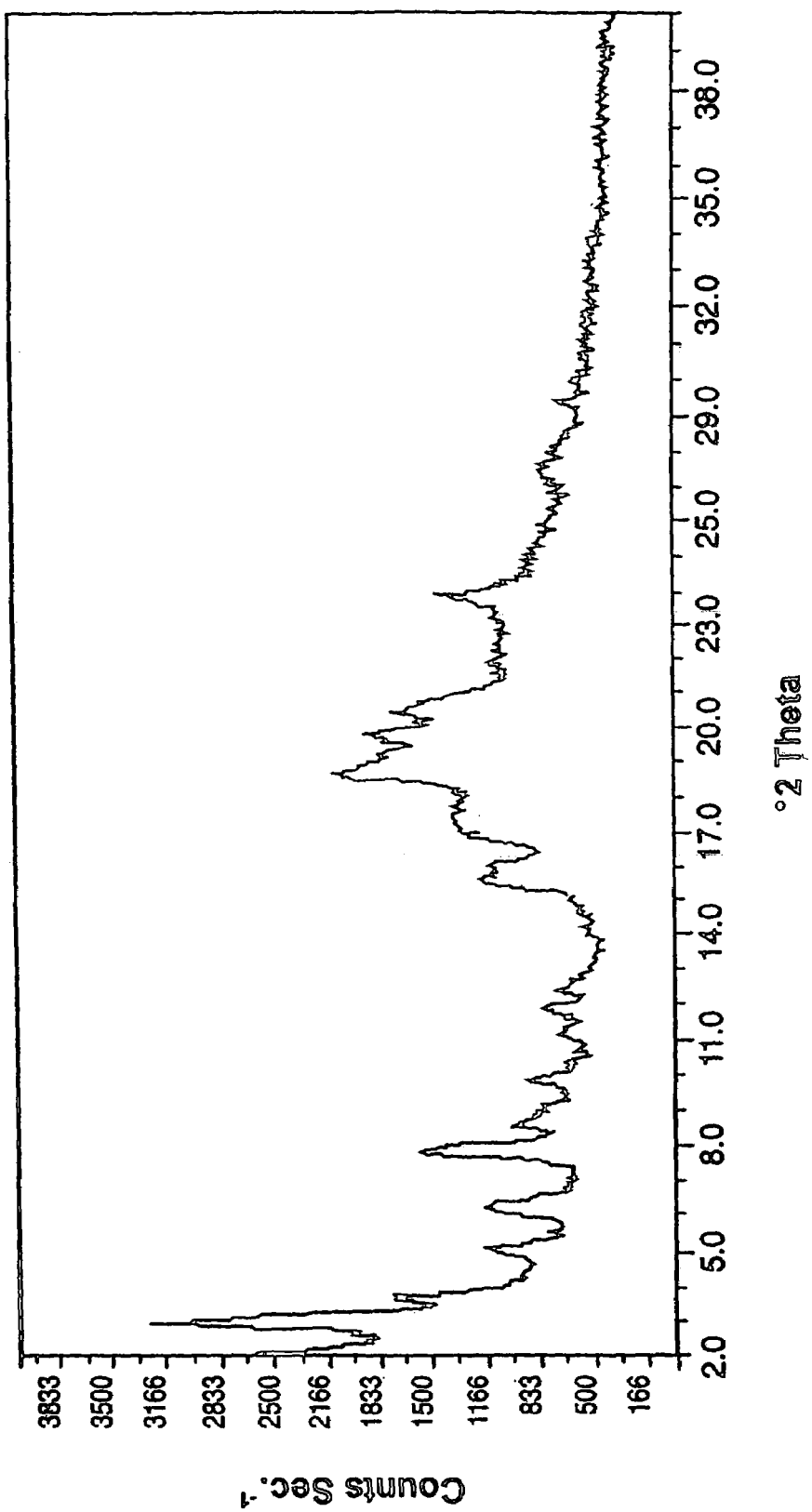
FIG. 12 is a characteristic powder X-ray diffraction pattern of atorvastatin hemi-calcium Form XI obtained using a conventional X-ray generator with a copper anode.
Figure 13:
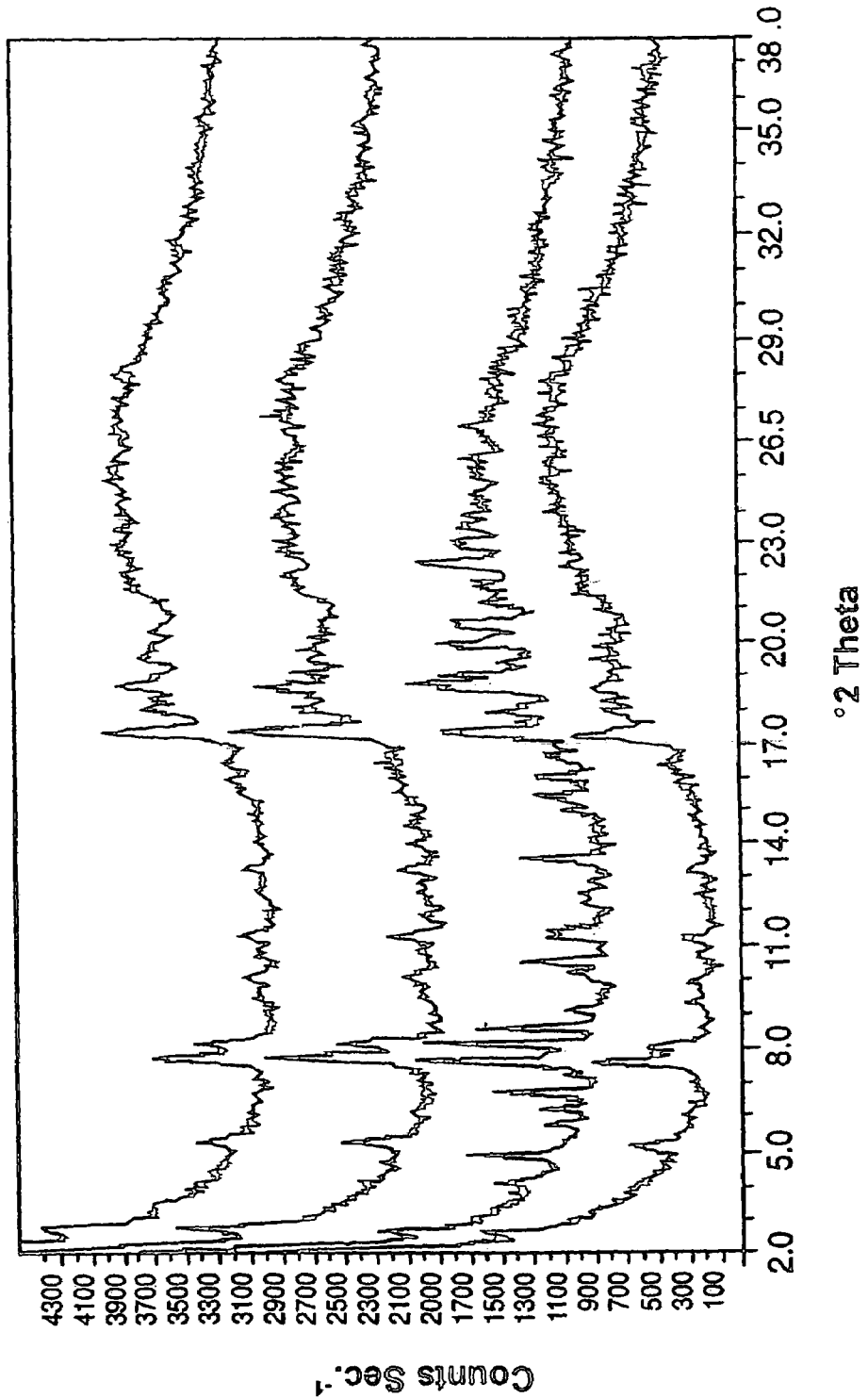
FIG. 13 is an overlay of typical powder X-ray diffraction patterns of atorvastatin hemi-calcium Form XII obtained using a conventional X-ray generator with a copper anode.

Atorvastatin hemi-calcium Form X produced the solid-state $^{13}C$ NMR spectrum shown in FIG. 11. Form X is characterized by the following solid-state $^3C$ nuclear resonance chemical shifts in ppm: 17.7, 18.7, 19.6, 20.6, 24.9, 43.4, 63.1, 66.2, 67.5, 71.1, 115.9, 119.5, 122.4, 126.7, 128.9, 134.5, 138.0, 159.4, 166.2, 179.3, 181.1, 184.3, 186.1. Form X is characterized by a solid-state $^{13}C$ nuclear magnetic resonance having the following chemical shifts differences between the lowest ppm resonance and other resonances: 1.0, 1.9, 2.9, 7.2, 25.7, 45.4, 48.5, 49.8, 53.4, 98.2, 101.8, 104.7, 109.0, 111.2, 116.8, 120.3, 141.7, 148.5, 161.6, 163.4, 166.6, 168.4. Characteristic parts of the pattern are found at 24-26 ppm (aliphatic range), 119-140 ppm (aromatic range) and other regions. The chemical shifts of Form X are averaged from three spectra taken of three samples of Form X. The values reported are within ±0.1 ppm, except for the carbonyl peak at 179. 3 ppm that is accurate within ±0.4 ppm.

Atorvastatin hemi-calcium Form X may be prepared by treating crystalline atorvastatin hemi-calcium, preferably Form V or Form I or mixtures thereof, or amorphous atorvastatin hemi-calcium with a mixture of ethanol and water, preferably in a ratio of about 5:1, at elevated temperature, preferably at reflux temperature, for a period of from about half an hour to a few hours, preferably about 1 h. The starting material may be added to the EtOH:water mixture at room temperature, followed by gradual heating of the suspension to reflux. Alternatively, the starting form of atorvastatin hemi-calcium may be added to the refluxing solvent mixture. In either case, the atorvastatin hemi-calcium should be observed to dissolve in the mixture and then reprecipitate in Form X. The ratio of atorvastatin hemi-calcium to the EtOH:water mixture preferably ranges from about 1:16 to about 1:25 (g:ml), more preferably from about 1:16 to about 1:21 (g:ml) and most preferably about 1:16 (g:ml). Form X may be collected by filtration shortly after cooling to room temperature or the suspension maybe stirred, for an addition period of from about 1 to about 20 hours, more preferably from about 3 to about 16 hours, before collecting the Form X.

Figure 9:
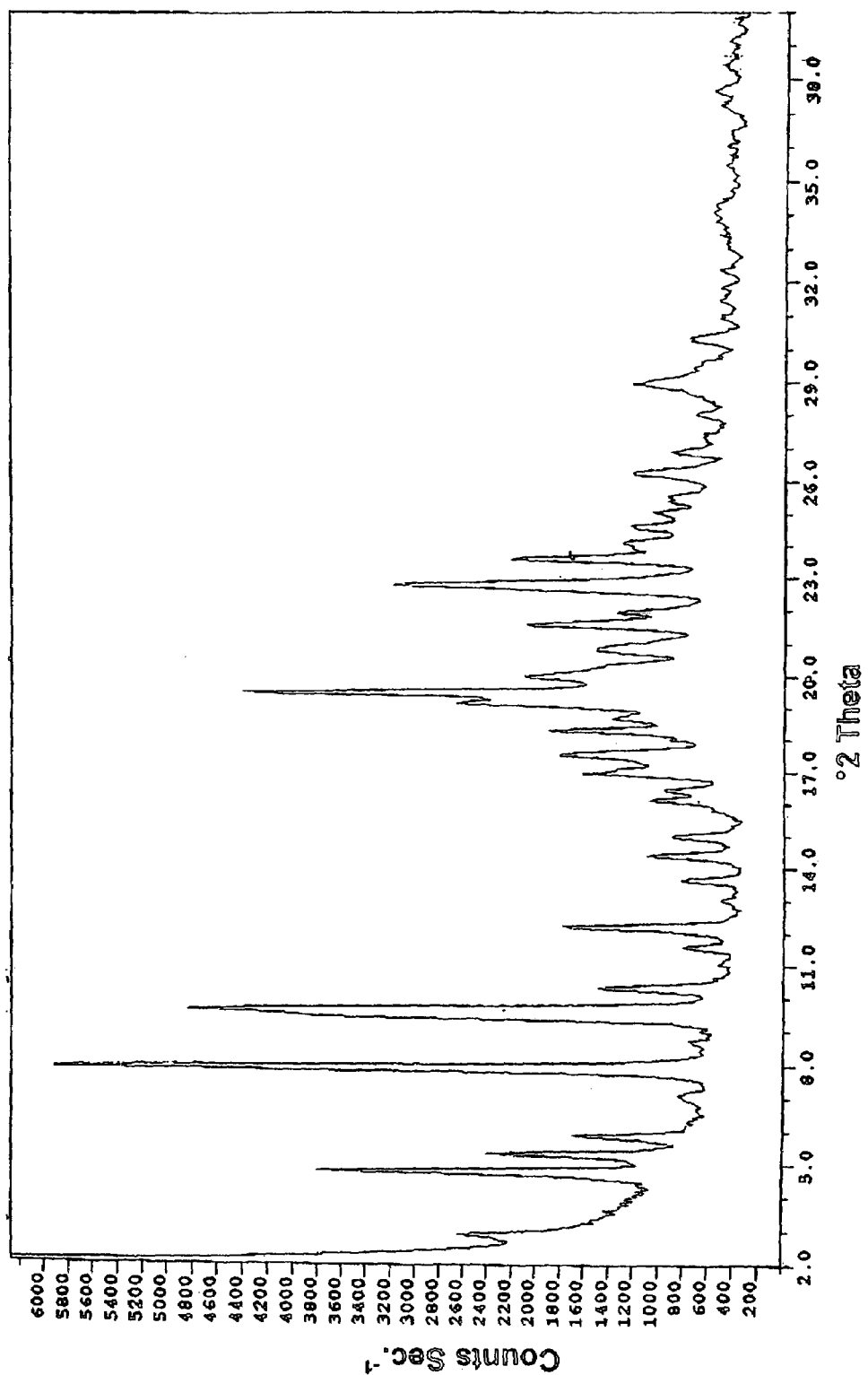
FIG. 9 is a characteristic powder X-ray diffraction pattern of atorvastatin hemi-calcium Form X obtained using a conventional X-ray generator with a copper anode.

Atorvastatin hemi-calcium Form XI is characterized by a powder X-ray diffraction pattern (FIG. 9) having peaks at 3.2, 3.7, 5.1, 6.3, 7.8, 8.6, 9.8, 11.2, 11.8, 12.4, 15.4, 18.7, 19.9, 20.5, 24.0±0.2 degrees two-theta.

Form XI may be obtained by suspending atorvastatin hemi-calcium Form V in methyl ethyl ketone ("MEK") at room temperature for a period of time sufficient to cause the conversion of Form V into Form XI.

Form XI also may be obtained by preparing a gel containing atorvastatin hemi-calcium in isopropyl alcohol and then drying the gel. The gel is best prepared by saturating isopropyl alcohol with atorvastatin hemi-calcium at reflux temperature and then cooling to room temperature. Extensive stirring at room temperature, as long as or more than 20 h, may be required in order for the gel to form. In the gel state, the solution is detectably more resistant to stirring and does not pour smoothly. The gel remains flowable in the sense that it can be stirred if sufficient force is applied and would not tear under such force.

Atorvastatin hemi-calcium Form XII is characterized by a powder X-ray diffraction pattern having peaks at 2.7, 8.0, 8.4, 11.8, 18.2, 19.0, 19.8, 20.7±0,2 degrees two-theta, and a halo that indicates the presence of amorphous material. Typical X-ray powder diffraction patterns of atorvastatin hemi-calcium Form XII are shown in FIG. 10.

Form XII may be prepared directly from the following compound

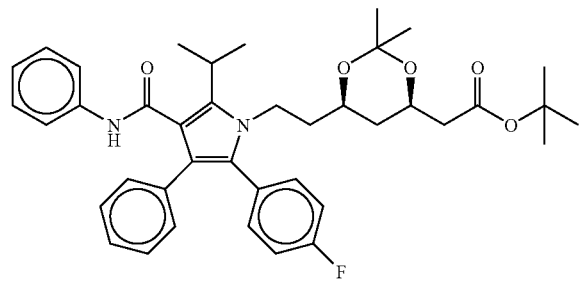

whose systematic chemical name is [R—(R*,R*)]-2-(4-fluorophenyl)-β,δ-dioxane-5-(1-methylethyl)-3-phenyl-4-[(phenylamino)carbonyl]-1H-pyrrole-1-tert-butylheptanoic ester, and which will hereafter be referred to as pyrrole acetonide ester or PAE. Form XII is prepared by first subjecting PAE to conditions that cleave the acetonide and tert-butyl ester group. Prefered conditions employ aqueous hydrochloric acid, more preferably about 1.5% aqueous hydrochloric acid. The solution of atorvastatin, in either free acid or lactone form, or mixture thereof, is then treated with calcium hydroxide, preferably a modest excess thereof, more preferably about 1.5 equivalents with, respect to the PAE. After association of the atorvastatin with dissolved calcium derived from the added hydroxide salt, any excess calcium hydroxide may be separated by filtration. One important feature of this process is the subsequent manipulation of the filtrate. Water is slowly added to the reaction mixture at mildly elevated temperature, preferably about 65° C. until atorvastatin hemi-calcium precipitates. At that point the temperature is increased until a clear solution is once again attained. The mixture is then allowed to cool resulting in the precipitation of atorvastatin hemi-calcium. The isolated precipitate is atorvastatin hemi-calcium Form XII.

The present invention also provides novel processes for preparing known forms of atorvastatin hemi-calcium.

Form I may be obtained by treating any form of atorvastatin hemi-calcium with water at room temperature to 100° C. for a period between a few to about 25 hours, preferably about 16 hours. Preferred starting materials are Forms V, VII, VIII, IX and X of atorvastatin hemi-calcium.

Form I also may be prepared by sonicating a suspension of atorvastatin hemi-calcium in ethanol, preferably absolute ethanol or in water, at between room temperature and the reflux temperature of the solvent for a period of a few minutes. Preferably between 1 and 3 minutes. Atorvastatin hemi-calcium Form VII is a preferred starting material though other forms may be used as well.

Form II may be prepared directly from [R—(R*,R*)]-2-(4-fluorophenyl)-β,δ-dioxane-5-(1-methylethyl)-3-phenyl4-[(phenylamino)carbonyl]-1H-pyrrole-1-tert-butylheptanoic ester (PAE) according to Example 31.

Atorvastatin hemi-calcium Form IV may be prepared by suspending Form I or Form V in 1-butanol for a period of time sufficient to complete the conversion of Form I or Form V to Form IV and then isolating Form IV from the mixture. The conversion may require a prolonged period depending on temperature and other conditions. The conversion typically takes about 24-72 hours at room temperature.

Form IV also may be obtained by suspending Form V in EtOH/H$_2$O at 50° C. for a period of time sufficient to cause the conversion of Form V to Form IV and then recovering Form IV from the suspensions. Prefered EtOH/4$_2$O mixtures contain about 15% H$_2$O.

Form IV also may be obtained by suspending atorvastatin hemi-calcium Form V in methanol for a period of time sufficient to cause the conversion of Form V to Form IV. The rate of conversion is sensitive to temperature and may take from about 1 to about 25 hours under typical laboratory conditions. The conversion requires about 16 hours, at room temperature. The conversion may be conducted at elevated temperature up to the reflux temperature of the solvent.

Form V may be prepared from PAE according to the process described with reference to the preparation of atorvastatin hemi-calcium Form XII. Form V may be obtained by drying Form XII at about 65°C for about 24 hours. The atorvastatin hemi-calcium Form V obtained in this manner is of high purity. However, it may be further purified by suspending in a mixture of about 10% water and about 90% ethanol and recovering Form V from the mixture in greater purity.

Amorphous atorvastatin hemi-calcium may be prepared by treating any.other form of atorvastatin hemi-calcium with acetone at room temperature to reflux temperature for between a few hours and 25 hours, preferably about 16 hours. A preferred starting material is Form V.

Amorphous atorvastatin hemi-calcium also may be prepared by sonicating any form of atorvastatin hemi-calcium in acetonitrile at any temperature between room temperature and the reflux temperature of acetonitrile. Sonicating for a few minutes, preferably from 1 to 3 minutes, is sufficient to transform the starting material into amorphous atorvastatin hemi-calcium. Preferred starting forms of atorvastatin hemi-calcium are Forms VII and I.

Amorphous atorvastatin hemi-calcium also may be prepared by ball milling of any crystalline form of atorvastatin hemi-calcium.

A further aspect of the present invention is a pharmaceutical composition and dosage form containing the novel forms of atorvastatin hemi-calcium.

The compositions of the invention include powders, granulates, aggregates and other solid compositions comprising novel Forms VI, VII, VIII, IX, X, XI and XII of atorvastatin-hemi-calcium. In addition, Forms VI, VII, VIII, IX, X, XI and XII solid compositions that are contemplated by the present invention may further include diluents, such as cellulose-derived materials like powdered cellulose, microcrystalline cellulose, microfine cellulose, methyl cellulose, ethyl cellulose, hydroxyethyl cellulose, hydroxypropyl cellulose, hydroxypropylmethyl cellulose, carboxymethyl cellulose salts and other substituted and unsubstituted celluloses; starch; pregelatinized starch; inorganic diluents like calcium carbonate and calcium diphosphate and other diluents known to the pharmaceutical industry. Yet other suitable diluents include waxes, sugars and sugar alcohols like mannitol and sorbitol, acrylate polymers and copolymers, as well as pectin, dextrin and gelatin.

Further excipients that are within the contemplation of the present invention include binders, such as acacia gum, pregelatinized starch, sodium alginate, glucose and other binders used in wet and dry granulation and direct compression tableting processes. Excipients that also may be present in a solid composition of Forms VI, VII, VIII, IX, X, XI and XII atorvastatin hemi-calcium further include disintegrants like sodium starch glycolate, crospovidone, low-substituted hydroxypropyl cellulose and others. In addition, excipients may include tableting lubricants like magnesium and calcium stearate and sodium stearyl fumarate; flavorings; sweeteners; preservatives; pharmaceutically acceptable dyes and glidants such as silicon dioxide.

The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The Dosages may be conveniently presented in unit dosage form and prepared by any of the methods well-known in the art of pharmacy.

Dosage forms include solid dosage forms, like tablets, powders, capsules, suppositories, sachets, troches and losenges as well as liquid suspensions and elixirs. While the description is not intended to be limiting, the invention is also not intended to pertain to true solutions of atorvastatin hemi-calcium whereupon the properties that distinguish the solid forms of atorvastatin hemi-calcium are lost. However, the use of the novel forms to prepare such solutions (e.g. so as to deliver, in addition to atorvastatin a, solvate to said solution in a certain ratio with a solvate) is considered to be within the contemplation of the invention.

Capsule dosages, of course, will contain the solid composition within a capsule which may be made of gelatin or other conventional encapsulating material. Tablets and powders may be coated. Tablets and powders may be coated with an enteric coating. The enteric coated powder forms may have coatings comprising phthalic acid cellulose acetate, hydroxypropylmethyl-cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents. A coated tablet may have a coating on the surface of the tablet or may be a tablet comprising a powder or granules with an enteric-coating.

Preferred unit dosages of thepharmaceutical compositions of this invention typically contain from 0.5 to 100 mg of the novel atorvastatin hemi-calcium Forms VI, VII, VIII, IX, X, XI and XII or mixtures thereof with each other or other forms of atorvastatin hemi-calcium. More usually, the combined weight of the atorvastatin he mi-calcium forms of a unit dosage are from 2.5 mg. to 80 mg.

Having thus described the various aspects of the present invention, the following examples are provided to illustrate specific embodiments of the present invention. They are not intended to be limiting in any way.

EXAMPLES

General

Absolute ethanol containing less than 0.2% water was purchased from Biolab®. Other reagents were reagent grade and were used as received.

Ball milling was performed using a Retsch centrifugal ball-mill S-100 equipped with a 250 ml stainless steal milling chamber and twenty seven 10 mm diameter stainless steal balls as milling media.

Preparation of Atorvastatin Hemi-Calcium Form VI

Example 1

Atorvastatin hemi-calcium Form I (1 g) was dissolved in acetone (9 ml) at room temperature and stirred for 2.5 hours. Then, water (8.5 ml) was added to get a precipitation and the mixture was then stirred for another 2.5 hours. The white solid was then filtered and dried at 50° C. for 5 hrs to obtain atorvastatin hemi-calcium Form VI (0.88 g, 88%).

Preparation of Atorvastatin Hemi-Calcium Form VII

Example 2

Atorvastatin hemi-calcium Form V (1.00 g) was stirred in absolute EtOH (400 ml) at room temperature for 16 h. The solid was collected by filtration and dried at 65° C. for 24 h to give atorvastatin hemi-calcium Form VII (40 mg, 40%).

Example 3

Atorvastatin hemi-calcium Form I (75 mg) was stirred in absolute EtOH (30 ml) at room temperature for 16 h. The solid was collected by filtration and dried at 65° C. for 24 h to give atorvastatin hemi-calcium Form VII (0.60 g, 80%).

Preparation of Atorvastatin Hemi-Calcium Form VIII

Example 4

To a flask equipped with a magnetic stirrer 1.0 g ($1.59 \times 10^{-3}$ mole) of [R—(R* R*)]-2-(4-fluorophenyl)-β,δ-dioxane-5-(1-methylethyl)-3-phenyl-4-[(phenylamino)carbonyl]-1H-pyrrole-1-tert-butylheptanoic ester were put in suspension in a 90% aqueous solution of acetic acid (10 ml). The reaction mixture was heated to 50° C. for three hours and then stirred at room temperature until the reaction was complete as determined by HPLC. The solvent was evaporated and the traces of acetic acid were removed by azeotropic distillation with toluene (3×100 ml) to obtain an oil with some toluene. This oil was dissolved in EtOH (10 ml) and water (2 ml). Then 5.5 eq.($8.4 \times 10^{-3}$ mole, 622 mg) of Ca(OH)$_2$ and tetrabutyl ammonium bromide. (5%, 0.05 g) were added. The reaction mixture was heated at 50° C. for 5 hours until the reaction was complete according to HPLC. Then a hot filtration was done under vacuum to remove the excess of Ca(OH)$_2$. The reaction mixture was then cooled to room temperature. To this solution water (50 ml) was added while stirring. The white precipitate was stirred at RT overnight, filtered under vacuum and dried at 65° C. for 18 hours to give 145 mg (16%) of atorvastatin hemi-calcium salt Form VIII.

Example 5

Atorvastatin hemi-calcium Form I (1 g) was slurried in absolute EtOH (80 ml), under reflux, for 24 hrs. The white solid was then filtered and dried at 65° C. for 20 hrs to obtain atorvastatin hemi-calcium Form VIII (0.85 g, 85%).

Example 6

Atorvastatin hemi-calcium Form I (1 g) was poured in boiling absolute EtOH. (40 ml). The compound began first to get soluble and then precipitate again. To this mixture was added MeOH (20 ml). The white solid was then filtered and dried at 50° C. for 20 hrs in a vacuum oven to obtain atorvastatin hemi-calcium Form VIII (188 mg, 19%).

Example 7

A suspension of 1.0 g of Atorvastatin hemi-calcium salt Form V in 1-Butanol (4 ml) and $H_2O$ (16 ml) was heated to reflux temperature for 1 hr. The mixture was then cooled to room temperature and stirred at this temperature for additional 16 hrs. The solid was filtered and dried at 50° C. in a vacuum oven for 16 hrs to give 0.9 g (91%) of Atorvastatin hemi-calcium salt Form VIII.

Example 8

5.0 g of Atorvastatin hemi-calcium salt Form V were added to a boiled solution of Ethanol 96% (150 ml). The mixture was refluxed for 2.5 hrs. Then it was cooled to 20° C. during 1.5 hrs, and stirred at this temperature for additional 16 hrs. The solid was filtered, washed with Ethanol 96% (2×25 ml) and dried at 65° C. for 20 hrs to give 4.4 g (88%) of Atorvastatin hemi-calcium salt Form VIII. During this process chemical purification occurs, so this process is good also for purification.

Example 9

5.0 g of Atorvastatin hemi calcium salt Form V, with a level of 0.12% of Des-fluoro Atorvastatin, were added to a boiled solution of Ethanol 96% (150 ml). The mixture was refluxed for 2.5 hrs. Then it was cooled to 20° C. during 1.5 hrs and stirred at this temperature for additional 16 hrs. The solid was filtered, washed with Ethanol 96% (2×25 ml) and dried at 65° C. for 20 hrs to give 4.4 g (88%) of Atorvastatin hemi calcium salt with a level of 0.06% of Des-fluoro Atorvastatin. Atorvastatin is obtained in Form VIII by this procedure.

Example 10

Atorvastatin hemi-calcium Form V (5 g) in absolute EtOH (35 ml) was refluxed for 2.5 h. The reaction mixture was then cooled to room temperature and stirred for an additional 16 h. Absolute ethanol (15 ml) was then added and the suspension was filtered and the collected solids were dried at 65° C. for 20 h to yield atorvastatin hemi-calcium Form VIII (4.7 g, 94%).

Preparation of Atorvastatin Hemi-Calcium Form IX

Example 11

Atorvastatin hemi-calcium Form I (1 g) was slurried in 1-butanol (20 ml) under reflux for 30 minutes. The mixture was then cooled to room temperature. The white solid was then filtered and dried at 50° C. under vacuum for 20 hrs to yield atorvastatin hemi-calcium Form IX (0.94 g, 94%). KF=0.9.

Example 12

Atorvastatin hemi-calcium Form I (1 g) was slurried in 1-butanol (20 ml) under reflux for 30 minute. Then n-hexane (40 ml) was added for further precipitation and, the reaction mixture was stirred at room temperature for 2 hours. The white solid was then filtered and dried at 50° C. in a vacuum oven for 20 hrs to yield atorvastatin Form IX (0.96 g, 96%).

Example 13

Atorvastatin hemi-calcium Form I (1 g) was slurried in 1-butanol (20 ml) under reflux for 30 minute. Then, IPA (40 ml) was added for further precipitation and the reaction mixture was stirred at room temperature for 2 hours. The white solid was then filtered and dried at 50° C. for 20 hrs in a vacuum oven to yield atorvastatin hemi-calcium Form IX (0.94 g, 94%) containing 0.9% water by Karl Fisher analysis.

Example 14

Atorvastatin hemi-calcium Form VIII (800 mg) was stirred in absolute EtOH (320 ml) at room temperature for 16 h. The solid was collected by filtration and dried at 65° C. for 24 hours to give atorvastatin hemi-calcium Form IX (630 mg, 79%).

Example 15

A mixture of atorvastatin hemi-calcium Form V (2.00 g) and 1-butanol (40 ml) was refluxed at 118° C. for half an hour. The mixture was then cooled to room temperature and stirred for an additional 3 hours. The solid was then collected by filtration and dried at 65° C. for 24 hours to give atorvastatin hemi-calcium Form IX (1.83 g, 92%).

Example 16

Atorvastatin hemi-calcium Form VIII was stored under 100% relative humidity at room temperature for nine days. The resulting solid was identified as Form IX by powder X-ray diffraction analysis.

Example 17

1 g of Atorvastatin hemi-calcium salt form V in 1-BuOH (10 ml) and $H_2O$ (10 ml) was heated to reflux for 1 h. The mixture was then cooled to room temperature and stirred at this temperature for additional 16 hrs. Filtration and drying at 65° C. for 24 hrs gave 0.79 g (79%) of Atorvastatin hemi-calcium salt form IX.

Example 18

1 g of Atorvastatin hemi-calcium salt form V in, 1-BuOH (10 ml) and EtOH (10 ml) was heated to reflux for 1 h. The mixture was then cooled to room temperature and stirred at this temperature for additional 16% hrs. Filtration and drying at 65° C. for 24 hrs gave 0.98 g (98%) of Atorvastatin hemi-calcium salt form IX.

Preparation of Atorvastatin Hemi-Calcium Form X

Example 19

Atorvastatin hemi-calcium Form V (10.00 g) was suspended in a mixture of EtOH (135 ml) and water (24 ml) and heated to reflux for 1 h. The mixture was then cooled to room temperature and stirred for an addition 16 h. The solid was collected by filtration and dried at 65° C. for 24 h to give atorvastatin hemi-calcium Form X (8.26 g, 83%).

Example 20

Atorvastatin hemi-calcium Form V (1.00 g) in a mixture of EtOH (9 ml) and water (1.6 ml) was refluxed for 1 h. The mixture was cooled to room temperature and then stirred an additional 3 h. The solid was collected by filtration and dried at 65° C. for 24 h to give atorvastatin hemi-calcium Form X (0.80 g, 80%).

Preparation of Atorvastatin Hemi-Calcium Form XI

Example 21

1.0 g of Atorvastatin hemi-calcium salt Form V was stirred in Methylethyl ketone ("MEK") (5 ml) at room temperature for 24 hrs. The solid was then filtered, washed with MEK (2 ml) and dried at 65° C. for 20 hrs to give 0.5 g (50%) of Atorvastatin hemi-calcium salt Form XI.

Example 22

A suspension of 1.0 g of Atorvastatin hemi-calcium salt Form V in Iso-propyl alcohol ("IPA") (7 ml) was heated to reflux temperature for 1 hr. The mixture was then cooled to room temperature and stirred at this temperature for additional 20 hrs. A gelatinous product was obtained. After addition of IPA (3 ml) the gel was filtered and dried at 65° C. for 20 hrs to give 0.8 g (80%) of Atorvastatin hemi-calcium salt Form XI.

Preparation of Atorvastatin Hemi-Calcium Form XII

Example 23

To a cylindrical reactor equipped with a distillation apparatus and a mechanical stirrer, 20 g (30.6 mmole) of [R—(R*, R*)]-2-(4-fluorophenyl)-β,δ-dioxane-5-( 1-methylethyl)-3-phenyl-4-[(phenylamino)carbonyl]-1H-pyrrole-1-tert-butylheptanoic ester (=pyrrole acetonide ester=PAE) were put in suspension in 250 ml of absolute Ethanol and 50 ml of aqueous 1.5% Hydrochloric acid. The reaction mixture was heated to 40° C. for 9-11 hrs, while a continuous distillation of a mixture of Ethanol, Acetone and water, under reduced pressure (500-600 mbar), was performed. Make-up of absolute Ethanol was done every hour (35-40 ml.). After 9-11 hours there was a reduction in the level of PAE to below 0.1% (according to HPLC). Without any further treatment, $Ca(OH)_2$ (1.5 eq., 3.4 g) were added. The reaction mixture was heated to 70° C. for 4-5 hrs. Then the excess of $Ca(OH)_2$ was collected by filtration. To the hot filtrate (65° C.), 350 ml of water were added slowly (using a dosing pump) during ¾-1 hour at 65° C. During the addition of water Atorvastatin hemi-calcium salt precipitated. After the addition of water the reaction mixture was heated to reflux (84° C.) till a clear solution was obtained. Then the mixture was cooled to 20° C. during 3 hrs and was stirred at this temperature for an additional 12-16 hrs. The solid was then filtered to give 45.0 g of wet cake of Atorvastatin hemi-calcium salt crystal form XII.

Preparation of Known Atorvastatin Hemi-Calcium Form I

Example 24

Atorvastatin hemi-calcium Form V (1.00 g) was stirred in water (400 ml) at room temperature for 16 h. The solid was collected by filtration and dried at 65° C. for 24 hours to yield atorvastatin hemi-calcium Form I (0.7 g, 70%).

Example 25

A mixture of atorvastatin hemi-calcium Form VII (10.00 g) in water (100 ml) was refluxed for 2 h. The mixture was cooled to room temperature and stirred for an additional hour. The solid was collected by filtration and dried at 65° C. for 24 h to yield-atorvastatin hemi-calcium Form I (9.64 g, 96%).

Example 26

Atorvastatin hemi-calcium Form VIII (800 mg) was stirred in water (320 ml) at room temperature for 16 h. The solid was collected by filtration and dried at 65° C. for 24 h to yield atorvastatin hemi-calcium Form I (350 mg, 44%).

Example 27

Atorvastatin hemi-calcium Form X (1.0 g) was stirred in water (400 ml) at room temperature for 24 h. The solid was collected by filtration and dried at 65° C. for 24 h to yield atorvastatin hemi-calcium Form I (720 mg, 72%).

Example 28

Atorvastatin hemi-calcium Form IX (750 mg) was stirred in water (300 ml) at room temperature for 24 h. The solid was collected and dried at 65° C. for 20 h to give atorvastatin calcium Form I (420 mg, 56%).

Example 29

Atorvastatin hemi-calcium Form VII (1.00 g) was stirred in absolute EtOH (20 ml) at room temperature. The slurry was then placed into a sonicator for 1.5 min (energy=235 kJ, Amp.=50%) to obtain a clear solution. After addition of water (14 ml), a precipitate formed and the slurry was put in the sonicator for another 2 min. (energy=3.16 kJ, Amp.=50%) which caused the slurry to gel The gel was dried at 65° C. for20 h to give atorvastatin hemi-calcium Form I (0.50 g, 50%).

Example 30

Atorvastatin hemi-calcium Form VII (1.00 g) was stirred in water (200 ml) at room temperature. The slurry was then placed into a sonicator for 2 min. (energy=3.0 kJ, Amp.=50%) which caused the slurry to gel. The gel was dried at 65° C. for 20 h to yield atorvastatin hemi-calcium Form I (0.92 g, 92%).

Preparation of Known Atorvastatin Hemi-Calcium Form II

Example 31

To a cylindrical reactor equipped with a distillation apparatus and a mechanical stirrer, 20 g (30.6 mmole) of [R—(R*, R*)]-2-(4-fluorophenyl)-β,δ-dioxane-5-(1-methylethyl)-3-phenyl-4-[(phenylamino)carbonyl]-1H-pyrrole-1-tert-butylheptanoic ester (=pyrrole acetonide ester=PAE) were put in suspension in 135 ml of Methanol and 7.6 ml of aqueous 10% Hydrochloric acid. The reaction mixture was heated to 35° C. for 3 hrs, while a continuous distillation of a mixture of Methanol, Acetone and water under reduced pressure (820 mbar) was performed. Make-up of Methanol was done every ½ hour (35 ml). After 3 hrs the level of PAE reduced below 0.1% (according to HPLC). Without any further treatment, $Ca(OH)_2$ (1.5 eq., 3.4 g), water (5 ml) and Methanol (45 ml) were added. The reaction mixture was heated to 70° C. for 2 hrs. Then the excess of $Ca(OH)_2$ was collected by filtration and the $Ca(OH)_2$ cake was washed with Methanol (2×10 ml). To the filtrate, 300 ml of water were added slowly (using a dosing pump) during ¾ hour at 65° C. During the addition of water Atorvastatin hemi-calcium salt precipitated. After the addition of water the reaction mixture was heated to reflux temperature (78° C.) for ½ hour. Then the mixture was cooled to 20° C. during 3 hrs and was stirred at this temperature for additional 20 hrs. The solid was then filtered and dried at 65° C. for 48 hrs to give 16.9 g (96%) Atorvastatin hemi-calcium salt crystal form II. KF=3.2%

Preparation of Known Atorvastatin Hemi-Calcium Form IV

Example 32

Atorvastatin hemi-calcium salt Form I (1.0 g) was stirred in 9 ml of 1-butanol at room temperature for 24 hours. The white solid was then filtered and dried at 50° C. in a vacuum oven for 16 hours to obtain 0.83 g (83%) of atorvastatin hemi-calcium salt Form IV.

Example 33

Atorvastatin hemi-calcium salt Form V (1.0 g) was stirred in 20 ml of 1-butanol at room temperature for 72 hours. The white solid was then filtered and dried at 65° C. in an oven for 20 hours to obtain 0.82 g (82%) of atorvastatin hemi-calcium salt Form IV.

Example 34

Atorvastatin hemi-calcium salt form V (2.0 g) was stirred in a mixture of EtOH (18 ml) and water (3.2 ml) at 50° C. for 1 hour. The precipitate was then filtered and dried at 65° C. for 20 hours to obtain 1.60 g (80%) of atorvastatin hemi-calcium salt form IV.

Example 35

A mixture of atorvastatin hemi-calcium Form V (2.00 g) and methanol (20 ml) was refluxed for 1 hour. The mixture was cooled to room temperature and stirred for an additional 16 hours. The solid was collected by filtration and dried at 65° C. for 24 to give atorvastatin calcium Form IV (1.37 g, 56%).

Example 36

A mixture of atorvastatin hemi-calcium Form V (1.00 g) in methanol (10 ml) was stirred at room temperature for 20 hours. The solid was collected by filtration and dried at 65° C. for 24 hours to give atorvastatin hemi-calcium Form IV (0.25 g, 25%).

Preparation of Atorvastatin Hemi-Calcium Form V

Example 37

To a cylindrical reactor equipped with a distillation apparatus and a mechanical stirrer, 20 g (30.6 mmole) of [R—(R*, R*)]-2-(4-fluorophenyl)-β,δ-dioxane-5-(1-methylethyl)-3-phenyl-4-[(phenylamino)carbonyl]-1H-pyrrole-1-tert-butylheptanoic ester (=pyrrole acetonide ester=PAE) were put in suspension in 250 ml of absolute Ethanol and 50 ml of aqueous 1.5% Hydrochloric acid. The reaction mixture was heated to 40° C. for 9-11 hrs, while a continuous distillation of a mixture of Ethanol, Acetone and water, under reduced pressure (500-600 mbar), was performed. Make-up of absolute Ethanol was done every hour (35-40 ml.). After 9-11 hours there was a reduction in the level of PAE to below 0.1% (according to HPLC). Without any further treatment, $Ca(OH)_2$ (1.5 eq., 3.4 g) were added. The reaction mixture was heated to 70° C. for 4-5 hrs. Then the excess of $Ca(OH)_2$ was collected by filtration. To the hot filtrate (65° C.), 350 ml of water were added slowly (using a dosing pump) during ¼-1 hour at 65° C. During the addition of water Atorvastatin hemi-calcium salt precipitated. After the addition of water the reaction mixture was heated to reflux (84° C.) till a clear solution was obtained. Then the mixture was cooled to 20° C. during 3 hrs and was stirred at this temperature for an additional 20 hrs. The solid was then filtered to give 45.0 g of wet cake of Atorvastatin hemi-calcium salt crystal form XII. This solid was dried at 65° C. for 24 hrs to give 16.7 g (95%) Atorvastatin hemi-calcium salt crystal form V. KF=2.8%-6.6%.

Process for Purifying Atorvastatin Hemi-Calcium Form V

Example 38

5.0 g of Atorvastatin hemi-calcium salt Form V were added to a boiled aqueous solution of Ethanol 90% (150 ml). The mixture was refluxed for 2.5 hrs. Then it was cooled to 20° C. during 1.5 hrs and stirred at this temperature for additional 16 hrs. The solid was then filtered, washed with Ethanol 90% (2×25 ml) and dried at 65° C. for 20 hrs to give 3.4 g (68%) of Atorvastatin hemi-calcium salt Form V.

Preparation of Known Amorphous Atorvastatin Hemi-Calcium

Example 39

Atorvastatin hemi-calcium Form V (2.00 g) was stirred in acetone (14 ml) at room temperature in a closed flask for 16 h. After 2 hours, the mixture clarified. While continuing to stir at room temperature, a solid precipitated. The acetone was decanted and the solid was collected with a spatula and transferred to a drying oven and dried at 65° C. for 20 h to give amorphous atorvastatin hemi-calcium (1.85 g, 93%).

Example 40

Atorvastatin hemi-calcium Form VII (1.00 g) was stirred in acetonitrile (20 ml) at room temperature. The slurry was then sonicated for 2 min. (energy=2.5 kJ, Amp.=50%). After decantation the acetonitrile, the solid was dried at 65° C. for 20 h to give amorphous atorvastatin hemi-calcium (0.71 g, 71%).

Example 41

Atorvastatin hemi-calcium Form I (1.00 g) was stirred in acetonitrile (20 ml) at room temperature. The slurry was then placed into a sonicator for 2 min. (energy=2.5 kJ, Amp.=50%). After decanting the acetonitrile, the solid was dried at 65° C. for 20 h to give amorphous atorvastatin hemi-calcium (0.71 g, 71%).

Example 42

Atorvastatin hemi-calcium (108 g) and twenty seven 10 mm diameter stainless steel milling balls were loaded into the milling chamber of the ball mill. The chamber was weighed and the mill was balanced according to the weight. The mill was operated at 500 rpm with the mill's reversing system on for 0.5 hr. The build-up material was scraped from the chamber walls into the bulk, and the mill was again operated for 4 hr, with cleaning of build-up every 15 min. finally, the material was separated from the balls by sieving with 300 μm screen. The resulting material was analyzed by PXRD and found to be amorphous. The process was repeated using atorvastatin Forms I, V and VIII and in each instance amorphous atorvastatin hemi-calcium was obtained.

Having thus described the invention with reference to particular preferred embodiments and illustrated it with examples, those in the art may appreciate modifications to the invention as described and illustrated that do not depart from the spirit and scope of the invention as defined by the claims which follow.

What is claimed is:

1. A process for preparing atorvastatin hemi-calcium Form I comprising the steps of:
   a) suspending atorvastatin hemi-calcium Form V, Form VII, Form VIII, Form IX, or Form X in water for a period of time sufficient to convert the atorvastatin hemi-calcium Form V, Form VII, Form VIII, Form IX, or Form X into Form I and
   b) recovering Form I from the suspension.
2. The process of claim 1 where step a) comprises suspending Form V in water.
3. The process of claim 1 where step a) comprises suspending Form VII in water.
4. The process of claim 1 where step a) comprises suspending Form VIII in water.
5. The process of claim 1 where step a) comprises suspending Form IX in water.
6. The process of claim 1 where step a) comprises suspending Form X in water.
7. The process of claim 1 where step a) comprises suspending atorvastatin hemi-calcium Form V, Form VII, Form VIII, Form IX, or Form X in water at room temperature to 100° C. for a period between a few hours to about 25 hours.
8. The process of claim 7 where the period is about 16 hours.

* * * * *